US010578559B2

(12) United States Patent
Silvanto et al.

(10) Patent No.: US 10,578,559 B2
(45) Date of Patent: Mar. 3, 2020

(54) LIQUID CONTACT INDICATOR

(71) Applicant: Apple Inc., Cupertino, CA (US)

(72) Inventors: Mikael M. Silvanto, San Francisco, CA (US); Simon Regis Louis Lancaster-Larocque, San Jose, CA (US); Alix McCabe, Chadds Ford, PA (US); Sunita Venkatesh, San Francisco, CA (US); Yongping Zhu, Cupertino, CA (US)

(73) Assignee: APPLE INC., Cupertino, CA (US)

( * ) Notice: Subject to any disclaimer, the term of this patent is extended or adjusted under 35 U.S.C. 154(b) by 418 days.

(21) Appl. No.: 15/451,296

(22) Filed: Mar. 6, 2017

(65) Prior Publication Data

US 2017/0254760 A1 Sep. 7, 2017

Related U.S. Application Data

(60) Provisional application No. 62/304,102, filed on Mar. 4, 2016.

(51) Int. Cl.
*G01N 21/91* (2006.01)
*G01N 21/78* (2006.01)
*G01N 31/22* (2006.01)
*A61F 13/84* (2006.01)
*A61F 13/42* (2006.01)
*A61L 15/56* (2006.01)

(52) U.S. Cl.
CPC .............. *G01N 21/91* (2013.01); *A61F 13/42* (2013.01); *A61F 2013/422* (2013.01); *A61F 2013/8497* (2013.01); *A61L 15/56* (2013.01); *B32B 2307/726* (2013.01); *B32B 2555/02* (2013.01); *G01N 21/78* (2013.01); *G01N 31/222* (2013.01)

(58) Field of Classification Search
CPC .............. A61F 13/42; A61F 2013/8497; A61F 2013/422; A61L 15/56; B32B 2555/02; B32B 2307/726; G01N 31/222; G01N 21/78; G01N 21/91
USPC ............ 604/361; 206/459.1, 459.5; 116/200, 116/201, 206
See application file for complete search history.

(56) References Cited

U.S. PATENT DOCUMENTS 4,621,193 A * 11/1986 Van Hoye .............. G01N 21/91
250/302
8,210,032 B2 * 7/2012 Sanford ............... G01N 31/222
73/29.02

(Continued)

*Primary Examiner* — Nimeshkumar D Patel
*Assistant Examiner* — Tania Courson
(74) *Attorney, Agent, or Firm* — Dorsey & Whitney LLP

(57) ABSTRACT

An electronic device having an indication member for determining liquid exposure in an electronic device is disclosed. The indication member may include ink and a layer covering the ink. The layer may include a liquid-permeable layer that allows liquid to pass through the layer and contact the ink. In this regard, at least some of the ink may rise through the layer and to a top surface of the indication member. Although the ink may be exposed at the top surface, in some cases, the ink is visible or detectable when exposed to light from an ultraviolet light source. Also, the top surface may include a pattern or other indicia that is also visible or detectable when exposed to the light source. When the indication member is exposed to liquid, the pattern may be altered or disturbed in a location corresponding to an exposed portion of the indication member.

18 Claims, 19 Drawing Sheets

(56) References Cited

U.S. PATENT DOCUMENTS

| | | | | |
|---|---|---|---|---|
| 8,440,274 | B2* | 5/2013 | Wang | G01N 31/222 |
| | | | | 379/437 |
| 9,086,298 | B2* | 7/2015 | Wang | B32B 5/06 |
| 9,300,773 | B2* | 3/2016 | Mittleman | H04M 1/0274 |
| 2004/0254549 | A1* | 12/2004 | Olson | A61F 13/42 |
| | | | | 604/361 |
| 2008/0145611 | A1* | 6/2008 | Mess | G09F 3/0291 |
| | | | | 428/143 |
| 2011/0224638 | A1* | 9/2011 | Cohen | A61F 13/42 |
| | | | | 604/361 |

* cited by examiner

LIQUID CONTACT INDICATOR

CROSS-REFERENCE TO RELATED APPLICATION(S)

This application claims the benefit of priority to U.S. Provisional Application No. 62/304,102, filed on Mar. 4, 2016, and titled "LIQUID CONTACT INDICATOR," the disclosure of which is incorporated herein by reference in its entirety.

FIELD

The following description relates to an indicator for detecting liquid. In particular, the following description relates to an indicator placed in an electronic device. The indicator can determine whether liquid entered the electronic device.

BACKGROUND

An indicator may be used to determine the presence of water by, for example, changing its appearance. The indicator may be used in an electronic device to determine whether water enters (or has entered) the electronic device. However, indicators presently on the market are essentially "commoditized" products in that they are generally similar in appearance and composition, and readily available from several manufacturers. While the color of the indicator may change after water exposure, the indicators may be easily replaced. In this regard, when the indicator determines the electronic device as undergone liquid ingress, a user of the electronic device (or other third party) can simply replace the indicator with a new, unused indicator. As such, an electronic device manufacturer may not be able to determine whether the electronic device was exposed to water. This poses a potential problem for the manufacture in determining whether a warranty (related to liquid ingress) of the electronic device should be voided.

SUMMARY

In one aspect, an indication member for determining a presence of liquid in a consumer electronic device is described. The indication member may include a layer that includes a first surface and a second surface opposite the first surface. The layer may further include a porous region that allows passage of the liquid from the first surface to the second surface. The indication may further include an ink material disposed on the second surface. In this configuration, when the liquid passes to the second surface, at least some of the ink material migrates via the porous regions to the first surface such that the ink material is rendered visible by ultraviolet light.

In another aspect, an electronic device is described. The electronic device may include an enclosure that includes an opening. The electronic device may further include an indication member carried by the enclosure and configured to determine whether liquid passes through the opening. The indication member may include an ink material visible by light from ultraviolet light after the liquid contacts the indication member.

In another aspect, a method for detecting liquid ingress in an electronic device that includes an indication member that includes an ink material and a layer having a top surface that covers the ink material is described. The method may include providing an ultraviolet light to the indication member. The ink material may be detectable when exposed to the ultraviolet light and may be configured to rise to the top surface when exposed to the liquid ingress. The method may further include determining, based upon providing the ultraviolet light, whether the top surface includes the ink material.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The disclosure will be readily understood by the following detailed description in conjunction with the accompanying drawings, wherein like reference numerals designate like structural elements, and in which.

Figure 1A:
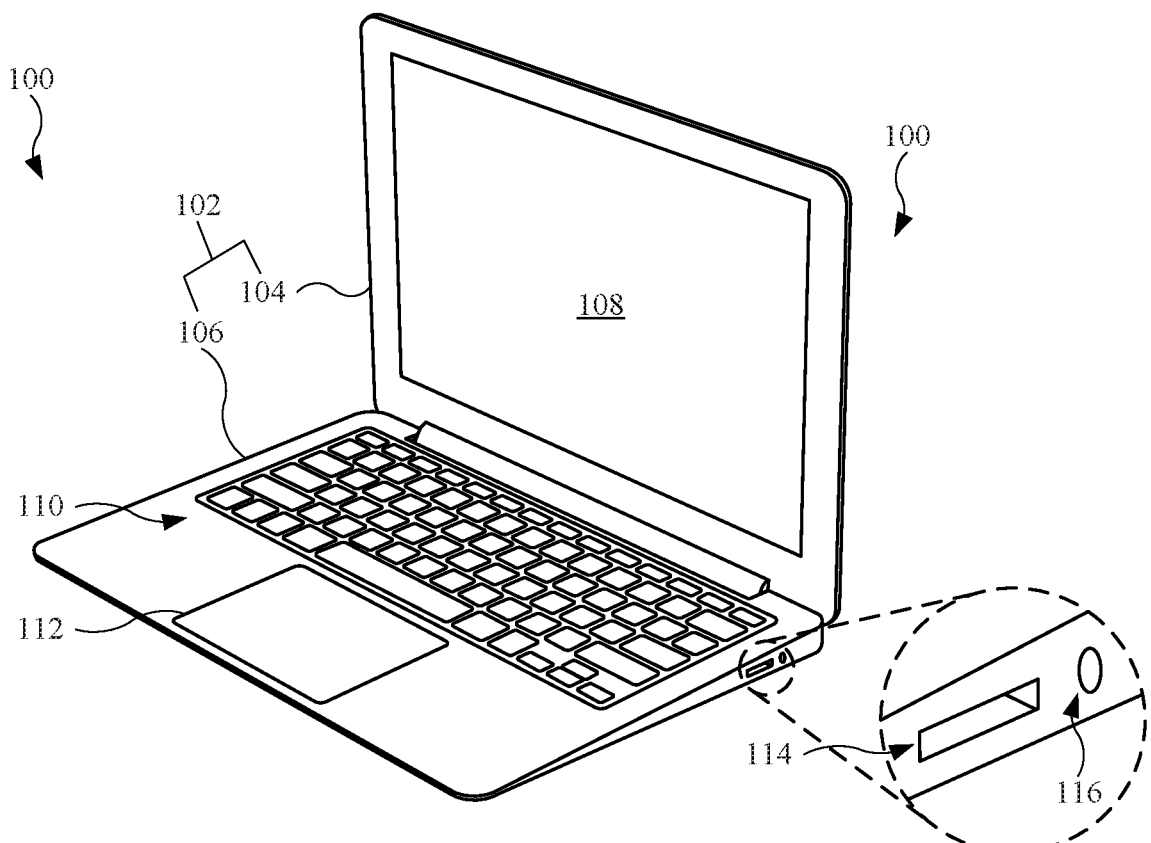
FIG. 1A illustrates an isometric view of an embodiment of an electronic device, in accordance with some described embodiments.

Those skilled in the art will appreciate and understand that, according to common practice, various features of the drawings discussed below are not necessarily drawn to scale, and that dimensions of various features and elements of the drawings may be expanded or reduced to more clearly illustrate the embodiments of the present invention described herein.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

In the following detailed description, references are made to the accompanying drawings, which form a part of the description and in which are shown, by way of illustration, specific embodiments in accordance with some described embodiments. Although these embodiments are described in sufficient detail to enable one skilled in the art to practice the described embodiments, it is understood that these examples are not limiting such that other embodiments may be used, and changes may be made without departing from the spirit and scope of the described embodiments.

The following disclosure relates to an indication member designed to alter or change its appearance in response to liquid exposure. The indication member, also referred to as a liquid contact indicator, may be placed in an electronic device, and accordingly, may be used to detect liquid ingress in an electronic device. The indication member may include multiple layers. For example, the indication member may include an ink layer and a cover layer disposed over the ink layer. In some instances, the cover layer includes an appearance (such as a color) that resembles one or more internal components of the electronic device, allowing the indication member to blend in with the internal component(s). The cover layer may be designed to interact with liquid (such as water). For example, in some embodiments, the cover layer includes a porous material that allows the liquid to pass through the cover layer. In other embodiments, the cover layer includes that dissolves when exposed to liquid. Accordingly, the layer may include a water-soluble or hydrophilic material. As a result of the liquid passing through the cover layer, the liquid may interact with the ink layer, thereby causing the ink layer to rise through the cover layer to a top surface of the indication member.

Although the ink layer may rise to the top surface, the ink material defining the ink layer may not be visible unless exposed to a light source. For example, the ink material may include a material that illuminates or glows when exposed to an ultraviolet ("UV") light source. By using a material that is generally invisible unless exposed to a particular light source, the indication member may hide or disguise whether the indication member is (or has been) exposed to liquid. Further, in some instances, the ink material may illuminate or glow only when exposed to a particular UV light source, such as a UV light source that emits light within a limited, predetermined wavelength (within the UV light range for wavelengths). In this manner, only light having the predetermined wavelength can be used to illuminate the ink material.

In other instances, the indication member may include an ink material disposed on the cover layer. Further, the ink material may be applied to the cover layer according to a predefined pattern, such as a grid, a symbol, a letter, logo, or the like. When the pattern is exposed to liquid, the pattern may be altered or disturbed. The ink material may also include UV-fluorescent ink visible only when exposed to light from a UV light source. In this regard, the pattern, including any alterations or disturbances to the pattern (from the liquid), may be visible when exposed the UV light.

Also, in some instances, the indication member may include an ink material designed to "bleed" when exposed to liquid. For example, the indication member may include additional ink material that is carried away by liquid that interacts with the ink material. In this regard, when the indication member is positioned in an electronic device, the ink material, displaced by the liquid, may provide feedback as to determine where liquid travels in the electronic device. Also, the ink material may include UV-fluorescent ink visible only when exposed to light from a UV light source.

Other indications members may be shown and described in the present disclosure that include an ink material that does not require UV light to view the ink material. For instance, an indication member may include a cover layer and ink layer. When the indication member is exposed to liquid, the ink material may interact with the cover layer, with the resultant interaction forming a visible indication that liquid is (or was) in contact with the indication member. The visible indication may include a contrast in color between the layer and a resultant mixture between the ink material and the cover layer.

Alternatively, an indication member may substitute an ink material with a mineral, such as bleached salts, that interact with one or more layers of the indication member, leaving a resultant visible indication that liquid is (or was) in contact with the indication member. In another alternative, an indication member may substitute an ink material for a hydrochromatic ink designed to change an appearance of the indication member when exposed to liquid. For example, prior to liquid exposure the hydrochromatic ink may include a color. However, when exposed to liquid, the color is removed and the hydrochromatic ink is essentially not visible. In this regard, the indication member may indicate liquid exposure based on an absence (or an apparent absence) of the hydrochromatic ink.

Also, in order to improve the performance of the indication member, the ink material described in this detailed description may undergo a "tuning" operation. In this regard, a composition that includes ink material can be optimized to prevent "false triggers" generated by the indication member. For example, the tuning operation to the composition of ink material may prevent the indication member from providing a false indication of liquid ingress into the electronic device. A "false trigger" may be caused by increased humidity, for example, as opposed to water in liquid form contacting the indication member. Also, the tuning operation may prevent leaching, or draining, of the ink material from the indication member prior to liquid exposure to the indication member.

The described embodiments of the indication members may include an adhesive layer designed to secure the indication member with an electronic device, or one of the components of the electronic device. Also, in some cases, a lowermost layer of the indication member may include adhesive properties that allow the indication member to adhesively secure with an electronic device, or one of the components of the electronic device.

These and other embodiments are discussed below with reference to FIGS. 1-44. However, those skilled in the art will readily appreciate that the detailed description given herein with respect to these Figures is for explanatory purposes only and should not be construed as limiting.

FIG. 1A illustrates an isometric view of an embodiment of an electronic device 100, in accordance with some described embodiments. In some embodiments, the electronic device 100 is a desktop computing device. In the embodiment shown in FIG. 1A, the electronic device 100 is a laptop computer device, or simply, a laptop. As shown, the electronic device 100 may include an enclosure 102. The enclosure 102 may be formed from a rigid material, such as a metal (including aluminum or aluminum alloy) or a durable plastic. As shown, the enclosure 102 includes a display housing 104 and a base portion 106. The display housing 104 may include a display 108 designed to provide visual information in the form of textual information, video images, and other forms of media images. The base portion 106 may include a keyboard assembly 110 and a touch pad 112, both of which are designed to provide an input or command to a processor or processors (not shown) to execute one or more instruction on a memory circuit (not shown) of the electronic device 100.

Also, the electronic device 100 may include several openings. For example, as shown in the enlarged view, the base portion 106 may include a first opening 114 and a second opening 116. In some embodiments, the first opening 114 is designed to receive an audio jack for an audio headset. Also, in some embodiments, the second opening 116 is designed to receive a connector that provides, for example, data and/or power to the electronic device 100.

Figure 1B:
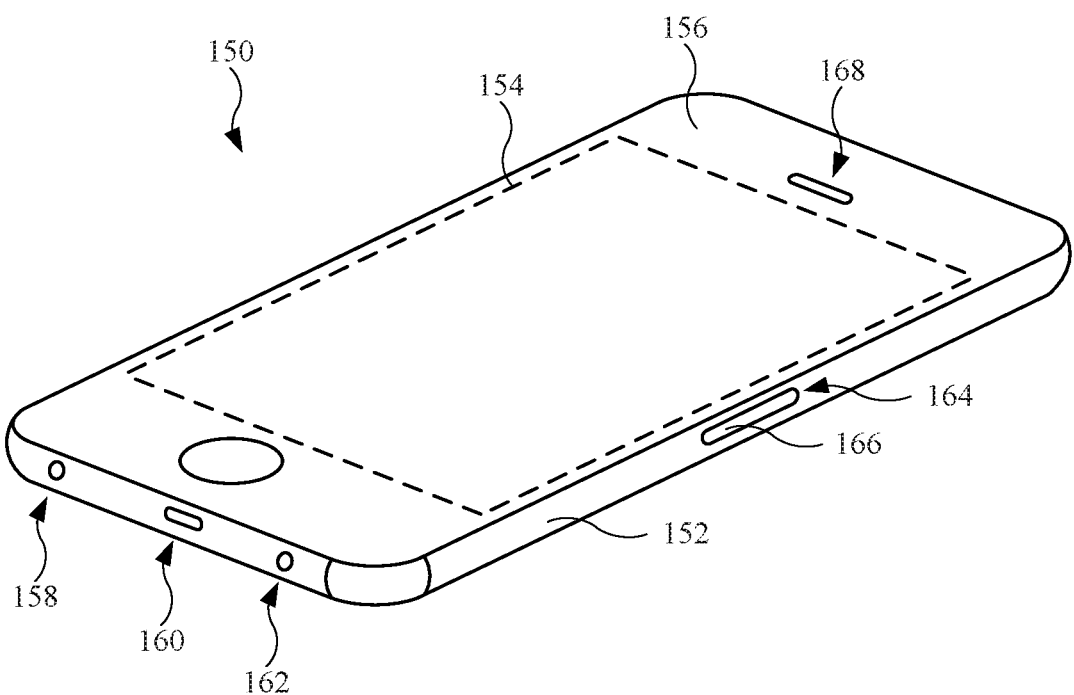
FIG. 1B illustrates an isometric view of an alternate embodiment of an electronic device, in accordance with some described embodiments.

FIG. 1B illustrates an isometric view of an alternate embodiment of an electronic device 150, in accordance with some described embodiments. In some embodiments, the electronic device 150 is a tablet computer device. In the embodiment shown in FIG. 1B, the electronic device 150 is a mobile wireless communication device, such as a smartphone. As shown, the electronic device 150 includes an enclosure 152 that defines an internal cavity to receive several operational components, such as a processor circuit and a memory circuit, as well as other components, such as a battery. The enclosure 152 may be formed from a rigid material, such as a metal (including aluminum or aluminum alloy) or a durable plastic. The electronic device 150 may also include a display assembly 154 (shown as a dotted line) designed to provide visual information in the form of textual information, video images, and other forms of media images. The display assembly 154 may include a touch sensitive capacitive layer that allows the electronic device 150 to receive a gesture or command by a capacitive coupling with the display assembly 154. The electronic device 150 may further include a protective layer 156 that covers the display assembly 154. As non-limiting examples, the protective layer 156 may include sapphire or glass.

The electronic device 150 may include several openings suitable for various user interactions. For example, the electronic device 150, and in particular the enclosure 152, may include a first opening 158, a second opening 160, and a third opening 162. The first opening 158 may be designed to receive an audio jack for an audio headset. The second opening 160 may be designed to receive a connector that provides data and/or power to the electronic device 150. The third opening 162 may be aligned with an audio speaker (not shown) disposed in the internal cavity of the enclosure. In this regard, the third opening 162 may allow acoustical energy in the form of audible sound to exit the electronic device 150. Also, the enclosure 152 may include an opening 164 designed to receive a subscriber identity module ("SIM") tray 166 that carries a SIM card (not shown) used to authenticate a user of the electronic device 150. Other features of the electronic device 150 may include openings. For example, the protective layer 156 may include an opening 168 aligned with a second audio speaker (not shown) to allow acoustical energy exit the electronic device 150.

While the openings of the electronic devices shown in FIGS. 1A and 1B may provide an enhanced user experience, each opening may provide a pathway for liquid ingress into the electronic devices. For example, referring to FIG. 1B, when the first opening 158 does not receive an audio jack, the first opening 158 may allow water to enter the electronic device 150. In some instances, a manufacturer of the electronic device 150 may warrant the use of the electronic device 150 provided, for example, there is no liquid ingress into the electronic device 150, as the liquid may cause damage to one or more operational components of the electronic device 150. In this regard, the electronic devices shown in FIGS. 1A and 1B may include features used to determine whether the electronic devices have undergone liquid ingress.

Figure 2:
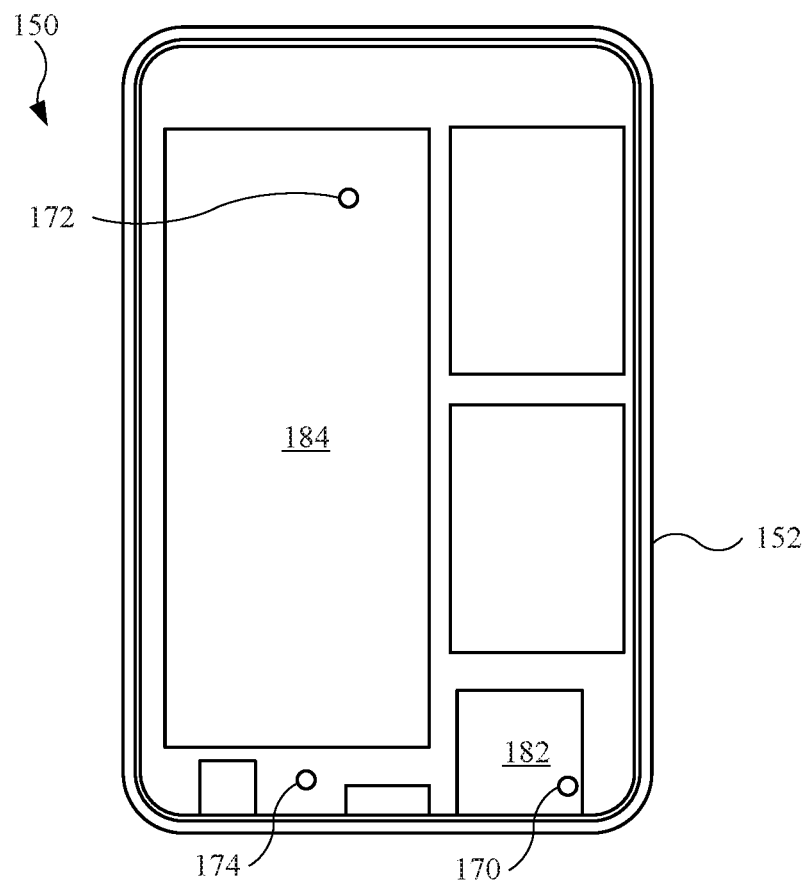
FIG. 2 illustrates a plan view of the electronic device shown in FIG. 1B, showing the electronic device having several indication members, with each indication member designed to detect liquid ingress in the electronic device.

For example, FIG. 2 illustrates a plan view of the electronic device 150 shown in FIG. 1B, showing the electronic device 150 having several indication members, with each indication member designed to detect liquid ingress in the electronic device 150. The protective layer 156 and the display assembly 154 are removed for purposes of illustration. As shown, the electronic device 150 may include a first indication member 170 located on a first internal component 182. The first internal component 182 may include, for example, an audio speaker. The electronic device 150 may further include a second indication member 172 located on a second internal component 184. The second internal component 184 may include, for example, a battery used to supply power to several internal components of the electronic device 150. Also, the electronic device 150 may further include a third indication member 174 located on an interior surface of the enclosure 152. Each indication member may be designed to change its appearance in response to liquid exposure. This will be described below. Also, the location of the first indication member 170, second indication member 172, and third indication member 174 shown in FIG. 2 are exemplary locations, and the location of the first indication member 170, second indication member 172, and third indication member 174 may vary in other electronic device. Also, the number of indication members may vary.

Figure 3:
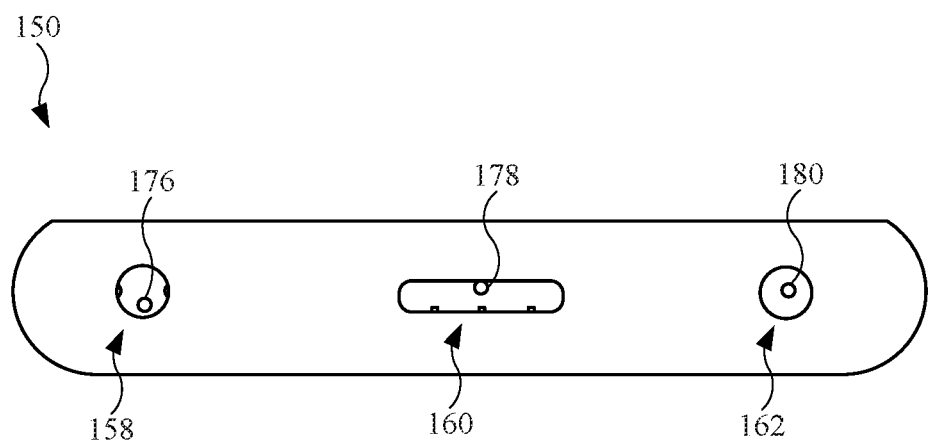
FIG. 3 illustrates a side view of the electronic device shown in FIG. 1B, showing indication members in several openings of the electronic device.

Further, the indication members, in accordance with some described embodiments, may vary in size to fit into other locations of the electronic device 150. For example, FIG. 3 illustrates a side view of the electronic device 150 shown in FIG. 1B, showing indication members in several openings of the electronic device 150. For example, the first opening 158 of the electronic device 150 may include a fourth indication member 176 designed to detect liquid ingress into the first opening 158. Similarly, the second opening 160 and the third opening 162 may include a fifth indication member 178 and a sixth indication member 180, respectively, with the indication members designed to detect liquid ingress into the respective openings. While a discrete number of indications members are shown, the number of indication members may vary. For example, in some embodiments (not shown), the second opening 160 includes two or more indication members.

Figure 4:
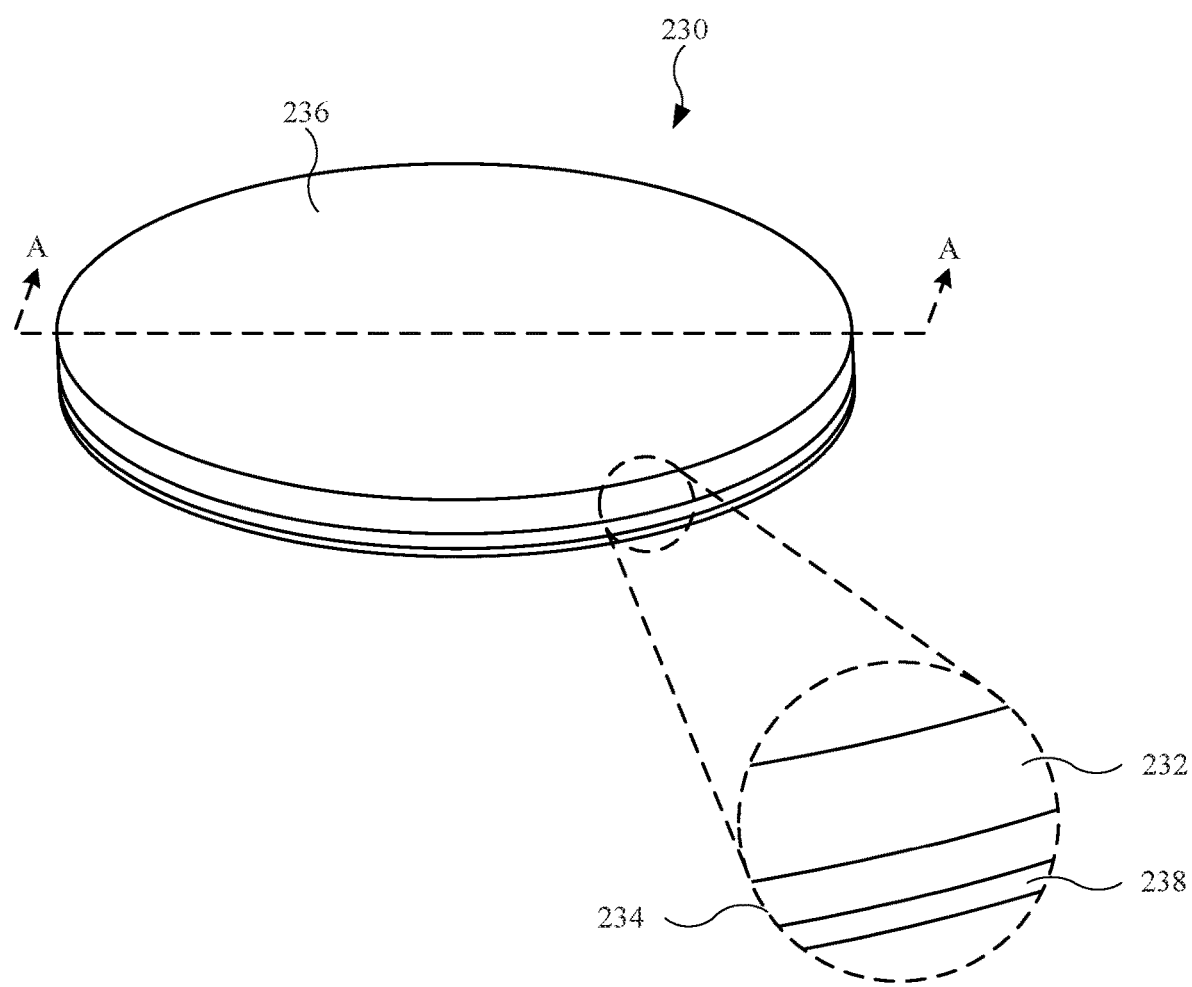
FIG. 4 illustrates an isometric view of an embodiment of an indication member, in accordance with some described embodiments.

FIG. 4 illustrates an isometric view of an embodiment of an indication member 230, in accordance with some described embodiments. The indication member 230 (and several indication members throughout this detailed description) may include a circular, or generally circular, shape. However, the shape of the indication member 230 (and indication members throughout this detailed description) may include a polygonal shape having three or more sides.

As shown in the enlarged view, the indication member 230 may include a first layer 232. The first layer 232 may be referred to as a cover layer, or uppermost layer of the indication member 230, as the first layer 232 may cover one or more layers of the indication member 230. In some embodiments, the first layer 232 includes a paper, or paper-like, material. In this regard, the first layer 232 may include a water-soluble or hydrophilic material designed to interact with liquid, allowing the liquid to pass through the first layer 232. Also, in some embodiments, the first layer 232 includes a color that matches that of a component or feature (not shown) onto which the indication member 230 is positioned. For example, when the component or feature is black or white, the first layer 232 may also include a black or white appearance, respectively, such that the indication member 230 blends in with the component or feature.

The indication member 230 may further include a second layer 234. In some embodiments, the second layer 234 includes an ink, or ink-based, material. The second layer 234 may be designed to extend, or rise, through the first layer 232 when the first layer 232 interacts with the liquid, causing a portion of the second layer 234 to rise to a first surface 236, representing an uppermost surface of the indication member 230. For example, the liquid may cause the first layer 232 to dissolve such that the liquid contacts the second layer 234, thereby causing the second layer 234 to occupy a portion (or portions) previously occupied by the first layer 232. Alternatively, the first layer 232 may include porous regions that allow the liquid to pass through the first layer 232 and contact the second layer 234 (when the second layer 234 is disposed on a surface of the first layer 232 and/or at least partially embedded in the first layer 232), thereby causing the second layer 234 to extend through the porous regions of the first layer 232. Also, while the second layer 234 is generally positioned across a second surface, or bottom surface (not shown), of the indication member 230, the second layer 234 may be scattered throughout certain areas to define a pattern. This will be shown below. As shown, the second layer 234 may be disposed on a surface of the first layer 232. However, in addition, at least a portion of the second layer 234 may be embedded in the first layer 232 such that a portion of the second layer 234 is embedded between opposing surfaces of the first layer 232.

Also, in some embodiments, the second layer 234 may be clear or transparent, and generally not visible (by a human eye). However, in some embodiments, the second layer 234 includes a UV-fluorescent material such that the second layer 234 glows or illuminates in response to exposure to light from a UV light source (not shown). In this regard, the second layer 234 may generally be detectable only when exposed to UV light. Further, the indication member 230 may not provide an indication that the indication member 230 is (or was) exposed to liquid unless the indication member 230 is exposed to the UV light. For example, the UV light source may illuminate portions of the second layer 234 (subsequent to liquid exposure to the indication member 230) that reach the first surface 236. This will be shown below. Also, the first layer 232 may provide a barrier that blocks UV light (from the light source) until the second layer 234 reaches the first surface 236. Also, the indication member 230 may include an adhesive layer 238 designed to adhesively secure the indication member 230 with an electronic device (not shown), or one of the internal components of the electronic device.

Figure 5:
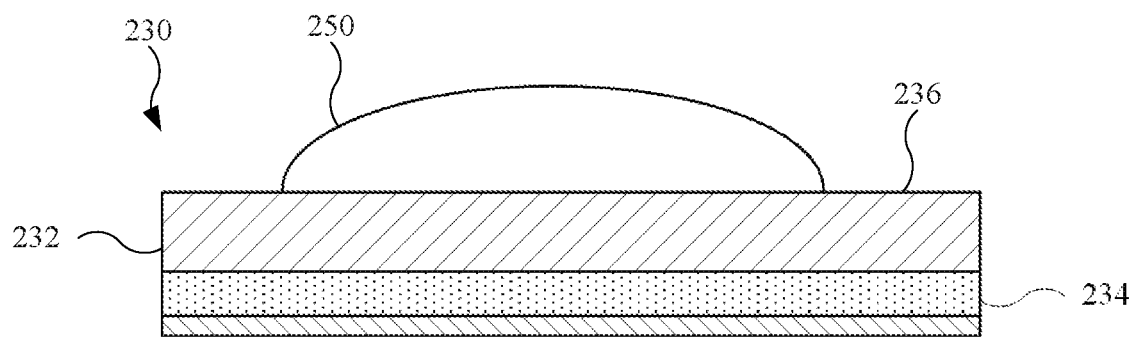
FIG. 5 illustrates a cross sectional view of the indication member shown in FIG. 4 taken along line A-A, further showing the indication member exposed to liquid.
Figure 6:
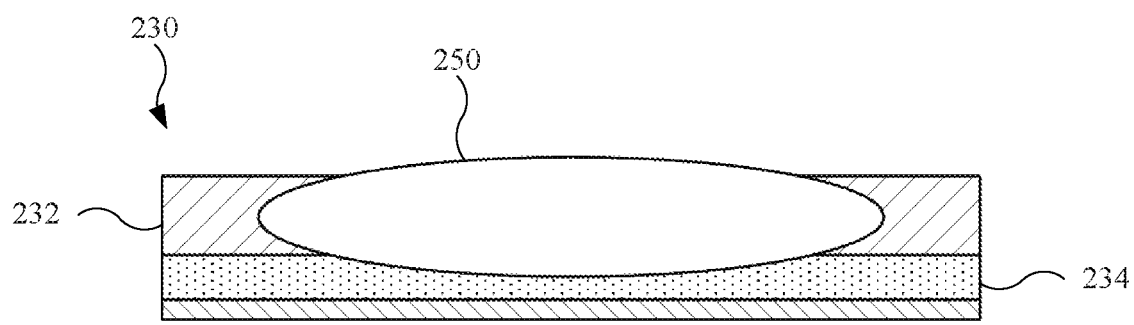
FIG. 6 illustrates a cross sectional view of the indication member shown in FIG. 5, showing the liquid penetrating through the first layer to engage the second layer.

FIG. 5 illustrates a cross sectional view of the indication member 230 shown in FIG. 4 taken along line A-A, further showing the indication member 230 exposed to liquid. As shown, liquid 250 contacts the first surface 236. Due in part to the aforementioned properties of the first layer 232, the liquid 250 passes through the first layer 232. For example, FIG. 6 illustrates a cross sectional view of the indication member 230 shown in FIG. 5, showing the liquid 250 penetrating the first layer 232 to engage the second layer 234. While FIG. 6 shows the liquid 250 passing through the first layer 232 as a "bulk" droplet, the liquid 250 may interact with the first layer 232, causing the first layer 232 to wet and/or dissolve (or at least partially dissolve). The interaction between the first layer 232 and the liquid 250 causes the liquid 250 to engage the second layer 234, which in turn, causes the second layer 234 to rise or extend, and occupy areas previously occupied by the first layer 232.

Figure 7:
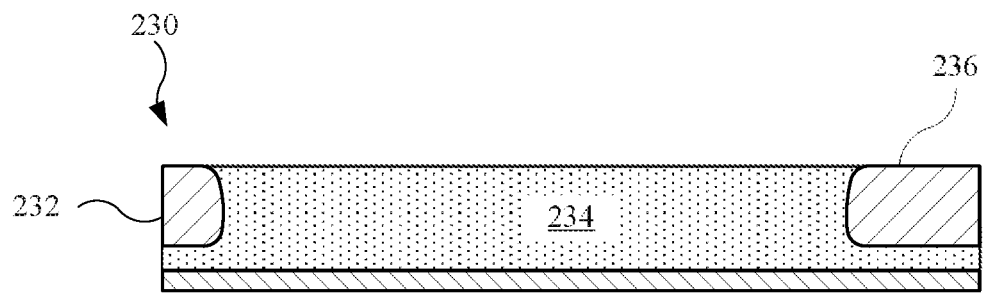
FIG. 7 illustrates a cross sectional view of the indication member shown in FIG. 6, showing the second layer passing through the first layer and extending to the top surface.

FIG. 7 illustrates a cross sectional view of the indication member 230 shown in FIG. 6, showing the second layer 234 passing through the first layer 232 and extending to the first surface 236. As shown, the second layer 234 may extend through the first layer 232 subsequent to interacting with the liquid 250 (shown in FIG. 6). Further, FIG. 7 shows portions of the second layer 234 rising to the first surface 236 in locations corresponding to the liquid exposure (from the liquid 250).

Figure 8:
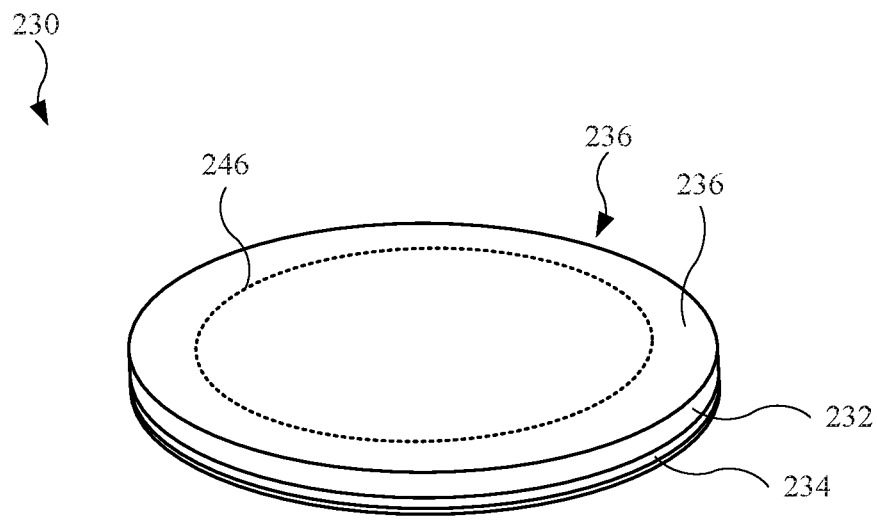
FIG. 8 illustrates an isometric view of the indication member shown in FIG. 7, with a dotted line indicating a location in which the second layer extends to the first surface.

In some cases, the second layer 234 may not be visible even when positioned on the first surface 236. As an example, FIG. 8 illustrates an isometric view of the indication member 230 shown in FIG. 7, with a dotted line 246 indicating a location in which the second layer 234 extends to the first surface 236. For example, the dotted line 246 represents a wetted portion (previously shown) of the first layer 232 as well as a resultant location of the second layer 234 rising to the first surface 236. Due in part to the nature of the second layer 234 being invisible, the second layer 234 may not be seen or detected by a human eye.

Figure 9:
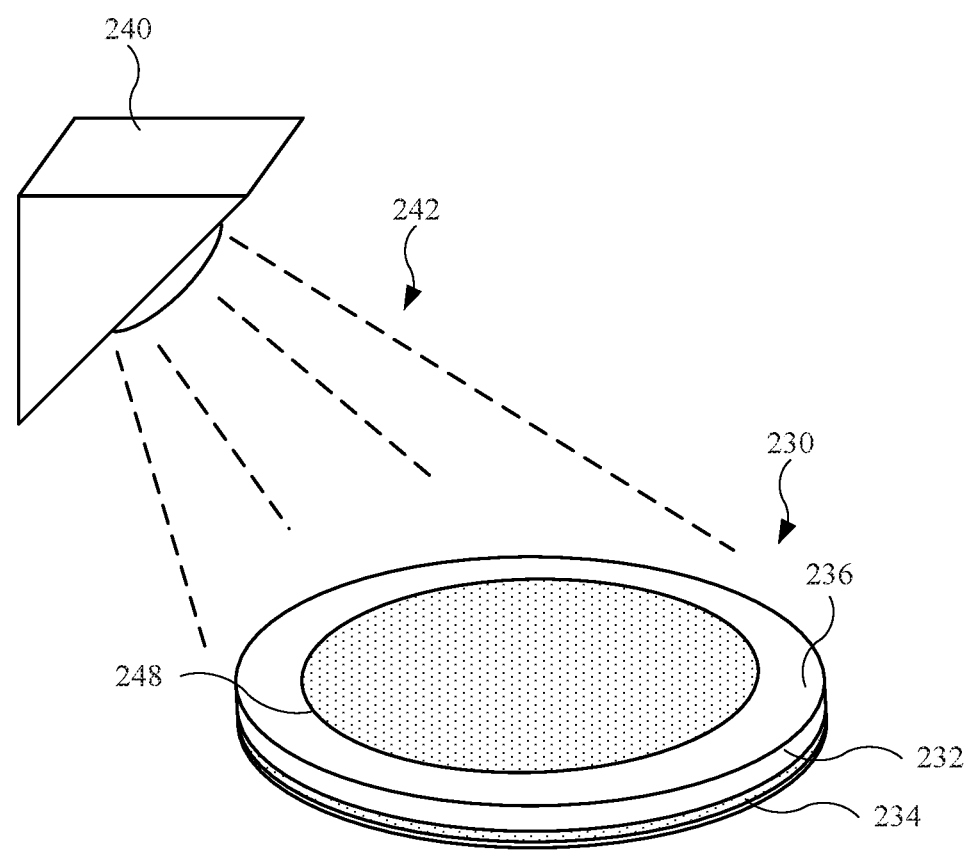
FIG. 9 illustrates an isometric view of the indication member shown in FIG. 8, with the indication member exposed to a light source.

However, when the second layer 234 includes a UV-fluorescent material, the second layer 234 may be visible when exposed to UV light. FIG. 9 illustrates an isometric view of the indication member 230 shown in FIG. 8, with the indication member 230 exposed to a light source 240. In some embodiments, the light source 240 is a UV light source that emits UV light 242 causing the second layer 234 to illuminate or glow. For example, an illuminated portion 248 (corresponding to the dotted line 246, shown in FIG. 8) of the second layer 234 may be illuminated and visible based on exposure from the UV light 242. In this manner, the indication member 230 may readily provide an indication that the indication member 230 has been exposed to liquid.

Also, in some embodiments, the second layer 234 includes UV-fluorescent material designed to illuminate or glow based on exposure to UV light having a predetermined wavelength (or a wavelength within a predetermine range of wavelengths). For example, UV light is known to include a wavelength approximately in the range of 10 nanometers (nm) to 400 nm. In some embodiments, the second layer 234 includes UV-fluorescent material designed to illuminate or glow only when exposed to UV light having a wavelength in the range of 10-200 nm. In other words, the second layer 234 may include UV-fluorescent material that does not illuminate or glow when exposed to UV light having a wavelength greater than 200 nm. In this manner, the indication member 230 may include UV-fluorescent material that requires an "authenticated" UV light, as the second layer 234 may not respond to UV light having a wavelength outside the predetermined range. Further, when the indication member 230 is installed in an electronic device (not shown), a manufacturer of the electronic device may install the indication member 230, and further be privy to the UV light required to illuminate the second layer 234 (subsequent to exposure by the indication member 230 to liquid). While an exemplary range of UV light is given, the range may differ according to the selected UV light source and UV-fluorescent material.

Also, although not shown, any portion of the first layer 232 may be exposed to liquid, and accordingly, any portion of the first surface 236 may include at least some of the second layer 23. Further, when the first surface 236 is entirely covered by liquid, the first layer 232 may interact with liquid, allowing the second layer 234 to occupy any portion previously occupied by the first layer 232.

Figure 10:
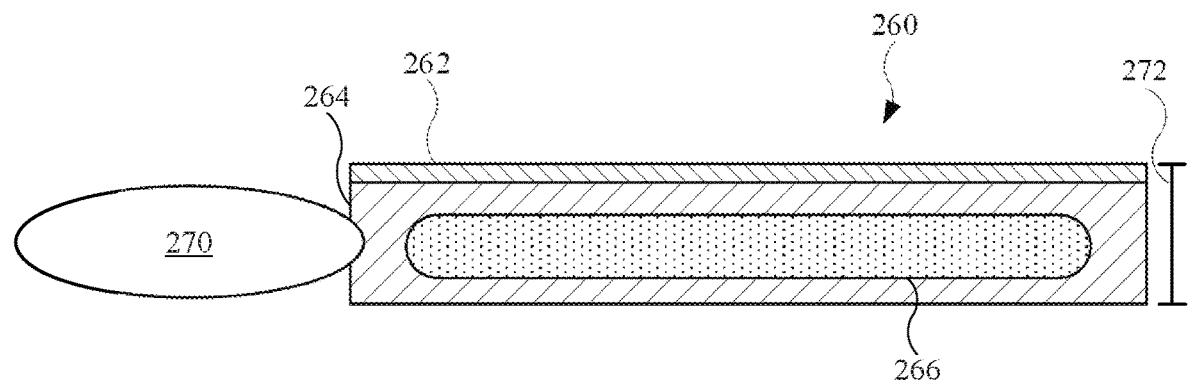
FIG. 10 illustrates a cross sectional view of an alternate embodiment of an indication member, showing the indication member having a layer embedded in another layer, and further showing liquid penetrating the indication member, in accordance with some described embodiments.

FIG. 10 illustrates a cross sectional view of an alternate embodiment of an indication member 260, showing the indication member 260 having a layer embedded in another layer, and further showing liquid 270 penetrating the indication member 260, in accordance with some described embodiments. As shown, the indication member may include a first layer 262 disposed on a second layer 264. Also, the second layer 264 may include a third layer 266 embedded in the second layer 264. The third layer 266 may include an ink material, including UV-visible ink. The indication member 260, when sufficient exposed to the liquid 270, may allow for the third layer 266 to extend or migrate to a lateral or side region of the indication member 260, causing the indication member 260 to change its appearance. This will be shown and discussed below.

In some embodiments, the first layer 262 includes a water-resistant layer. For example, the first layer 262 may include a polyethylene terephthalate ("PET") film. However, other water-resistant materials are possible. The first layer 262 may undergo a lamination process to attach or secure with the second layer 264. Due to the water-resistant characteristics, the first layer 262 may prevent liquid ingress from penetrating the indication member 260 in a location corresponding to an interface between the first layer 262 and the second layer 264. Accordingly, as shown in FIG. 10, the liquid 270 (generally represent moisture) may penetrate the indication member 260 by along the lateral or side regions of the indication member 260. Also, the first layer 262 may prevent the indication member from providing a "false trigger" of moisture detection. As an example, the first layer 262 may prevent relatively smaller amounts of moisture, due to increased humidity, from causing the indication member 260 to provide an indication of liquid ingress in an electronic device (not shown). This includes prevent the third layer 266 from migrating to the lateral regions of the indication member 260 when only humid air is present. In this regard, not only can the first layer 262 require the liquid 270 to pass through lateral or side regions of the indication member 260, but an amount of the liquid 270 greater than an amount to due moisture in ambient air may be required for the indication member 260 to provide an indication of liquid ingress.

Figure 11:
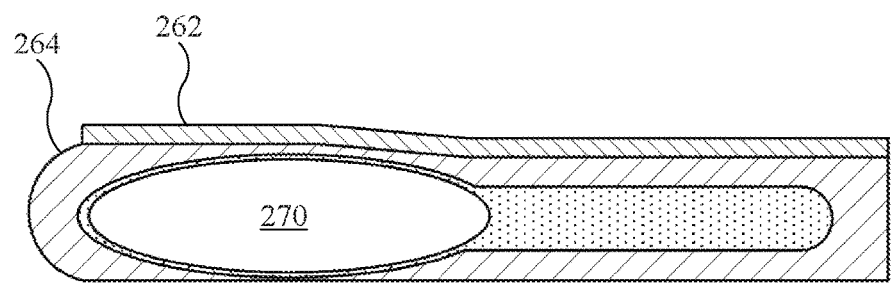
FIG. 11 illustrates a cross sectional view of the indication member shown in FIG. 10, showing the liquid further passing through the indication member.

In some embodiments, the second layer 264 includes a paper, or paper-like, material. In this regard, the second layer 264 may include a water-soluble or hydrophilic material designed to interact with liquid, allowing the liquid to pass through the second layer 264 (similar to the first layer 232, shown in FIG. 4). Further, in some embodiments, the second layer 264 may expand in multiple directions. For example, FIG. 11 illustrates a cross sectional view of the indication member 260 shown in FIG. 10, showing the liquid 270 further penetrating the indication member 260, and in particular, the second layer 264. As shown, the second layer 264 may expand, due to its material properties, radially outward (along the lateral or side regions) relative to the first layer 262. The radial expansion of the second layer 264 may provide an indication, by the indication member 260, of liquid ingress.

Figure 12:
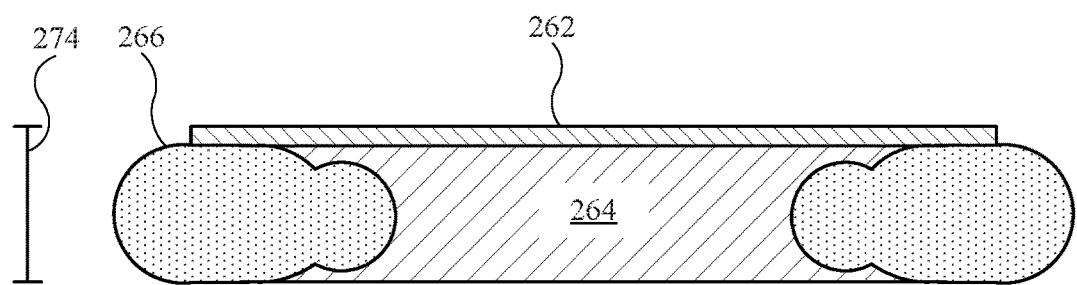
FIG. 12 illustrates a cross sectional view of the indication member shown in FIG. 11, subsequent to the liquid fully penetrating the second layer.

FIG. 12 illustrates a cross sectional view of the indication member 260 shown in FIG. 11, subsequent to the liquid 270 (shown in FIG. 11) fully penetrating the second layer 264. As a result of the liquid penetration, not only does the second layer 264 expand radially outward with respect to the first layer 262, but also the third layer 266 extends or migrates to the lateral or side regions of the second layer 264. In this regard, the indication member 260 may provide two forms of liquid indication, in the form of the second layer 264 expanding, and also in the form of the third layer 266 expanding to the lateral edge of the second layer 264. It should be noted that when the third layer 266 includes a UV ink material, the third layer 266 is visible when exposed to UV light from a UV light source (not shown).

Referring again to FIG. 10, the indication member 260 may include a dimension 272 associated with minimal or no liquid penetration. The dimension 272 may be associated with the height of the indication member 260, as defined in part by the first layer 262 and the second layer 264. However, once the second layer 264 absorbs the liquid 270 (as shown in FIG. 12), the indication member 260 may increase to a dimension 274 greater than the dimension 272 (shown in FIG. 10). Accordingly, the second layer 264 may expand in two dimensions: in a radially outward dimension, and a vertical direction (perpendicular to the radially outward direction). Furthermore, the amount of increase between the dimension 274 (shown in FIG. 12) and the dimension 272 (shown in FIG. 10) provides yet another indication of liquid ingress by the indication member 260.

Figure 13:
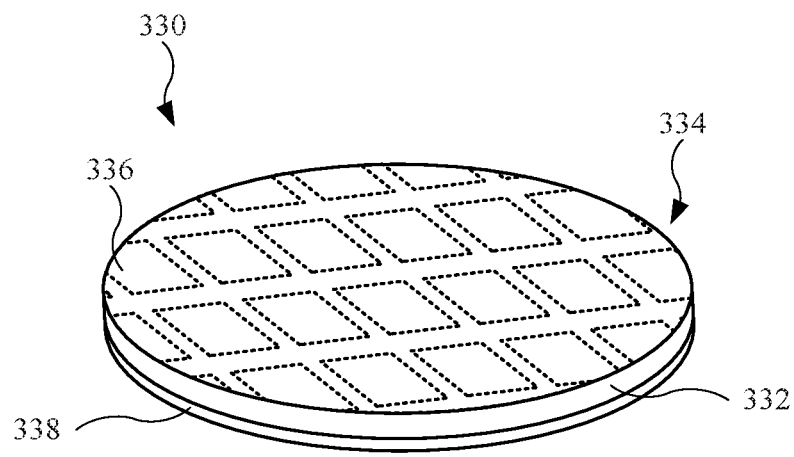
FIG. 13 illustrates an isometric view of an alternate embodiment of an indication member, in accordance with some described embodiments.

FIG. 13 illustrates an isometric view of an alternate embodiment of an indication member 330, in accordance with some described embodiments. As shown, the indication member 330 may include a first layer 332. The first layer 332 may include any feature or features previously described for a first layer 232. The indication member 330 may further include a second layer 334. The second layer 334, denoted as dotted lines, may include a UV-fluorescent material that is generally not visible unless exposed to UV light. In some embodiments (not shown), the first layer 332 covers the second layer 334, and portions of the second layer 334 may rise to a top surface 336 of the indication member when the first layer 332 is exposed to liquid. In the embodiment shown in FIG. 13, the second layer 334 is positioned on the top surface 336 prior to liquid exposure to the indication member 330. Also, the indication member 330 may include an adhesive layer 338 designed to adhesively secure the indication member 330 with an electronic device (not shown), or one of the internal components of the electronic device. Also, as shown, the second layer 334 may define a pattern. The pattern can include a unique pattern, such as a symbol, a letter, a logo, or some indicium associated with a manufacture of an electronic device that carries the indication member 330. However, in the embodiment shown in FIG. 13, the second layer 334 defines a pattern in the form of a grid.

Figure 14:
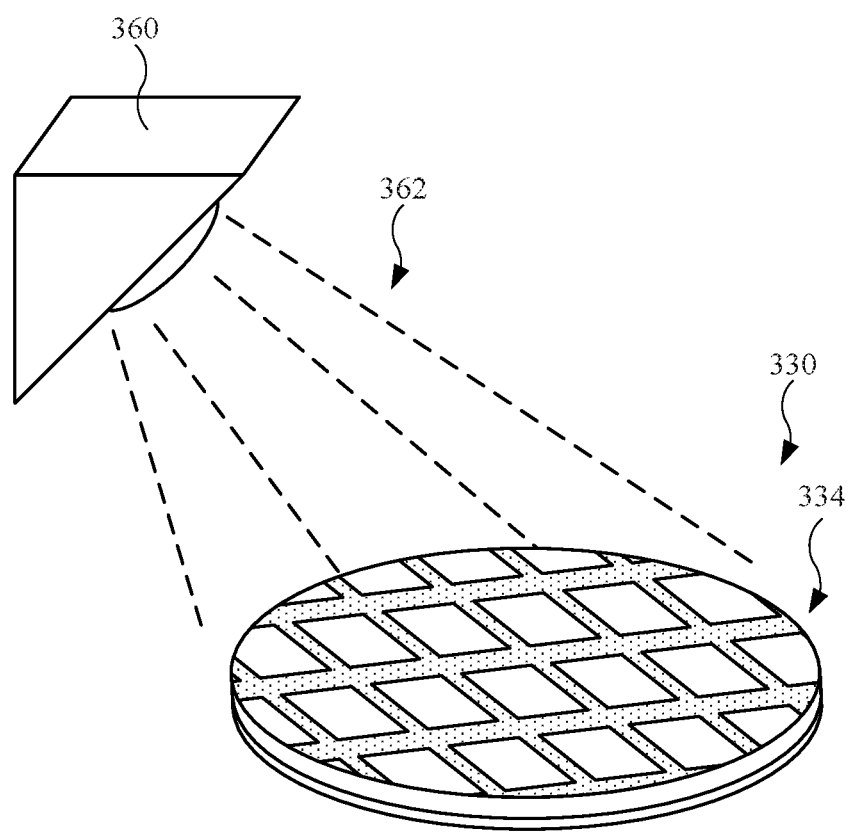
FIG. 14 illustrates an isometric view of the indication member shown in FIG. 13, with the indication member exposed to a light source.

FIG. 14 illustrates an isometric view of the indication member 330 shown in FIG. 13, with the indication member 330 exposed to a light source 360. The light source 360 may include a UV light source that emits UV light 362 causing the second layer 334 to illuminate or glow. Accordingly, the pattern defined by the second layer 334 may illuminate or glow when exposed to the UV light 362 such that the second layer 334 is now visible.

Figure 15:
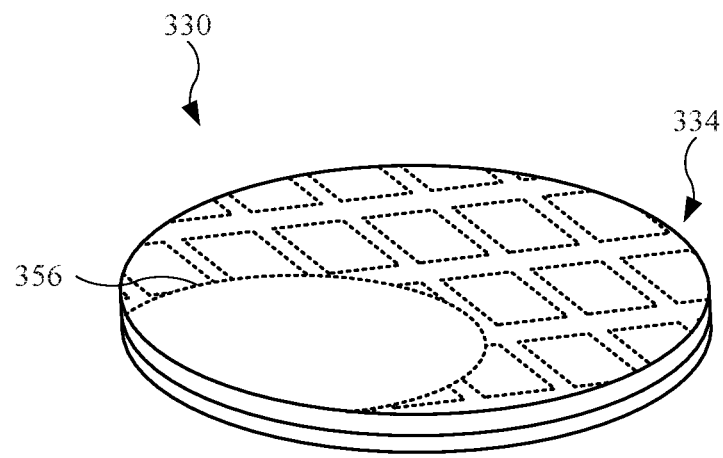
FIG. 15 illustrates an isometric view of the indication member shown in FIG. 14, subsequent to the indication member undergoing liquid exposure.

FIG. 15 illustrates an isometric view of the indication member 330 shown in FIG. 14, subsequent to the indication member 330 undergoing liquid exposure. As shown, the second layer 334, and in particular, the pattern defined by the second layer 334, may be altered or disturbed by the liquid. For example, the FIG. 15 shows liquid exposure, represented by a dotted line 356, with the liquid exposure altering the pattern of the second layer 334. Due in part to the generally invisible nature of the second layer 334, any alternations or disturbances to the second layer 334 may not be seen.

Figure 16:
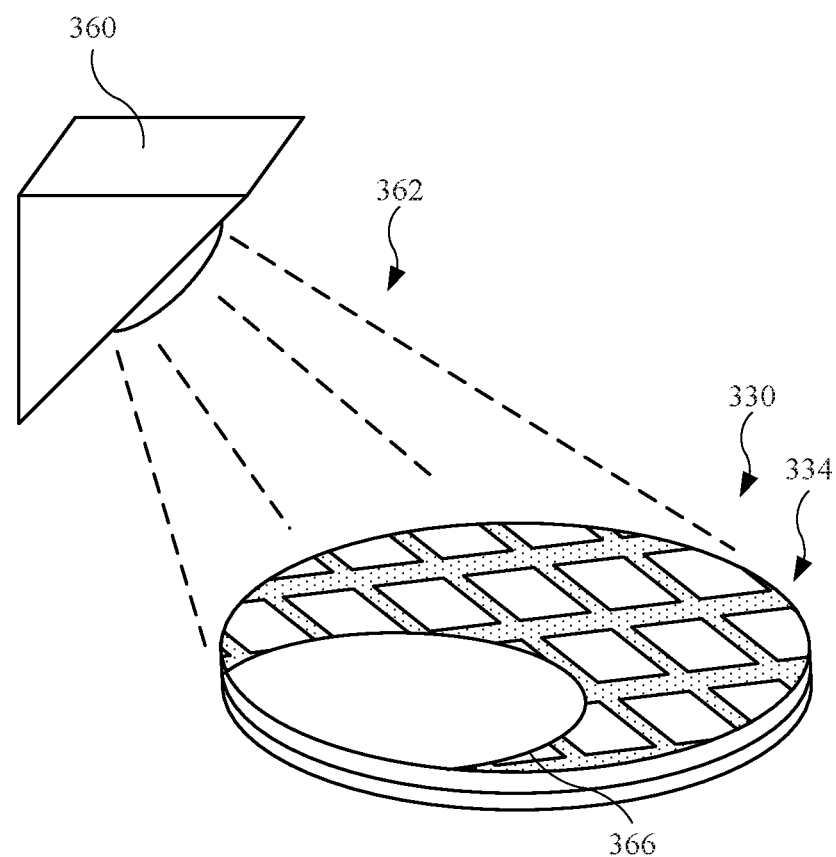
FIG. 16 illustrates an isometric view of the indication member shown in FIG. 15, showing the indication member exposed to the light source.

However, when the indication member 330, and in particular, the second layer 334, is exposed to UV light, the second layer 334 may be visible. For example, FIG. 16 illustrates an isometric view of the indication member 330 shown in FIG. 15, showing the indication member 330 exposed to the light source 360. As compared to FIG. 14, the pattern defined by the second layer 334 may be altered, defining an altered portion 366 that corresponds the liquid exposure to the second layer 334 (shown as the dotted line 356, in FIG. 15). In this manner, the indication member 330, and in particular, the alteration to the second layer 334, provides an indication that the indication member 330 has been exposed to liquid, while otherwise hiding the indication when the indication member 330 is not exposed to the UV light 362.

Figure 17:
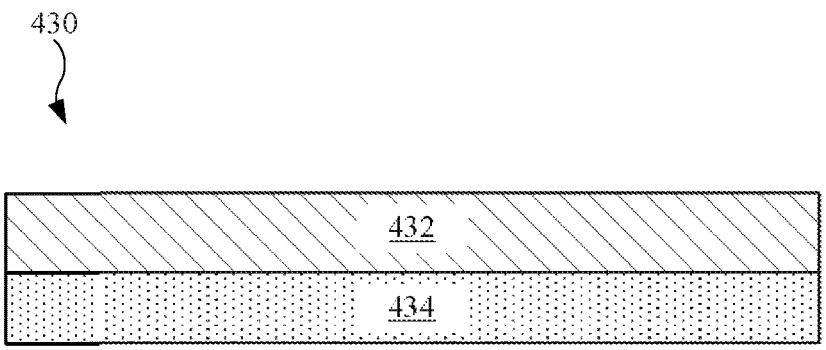
FIG. 17 illustrates a cross sectional view of an alternate embodiment of an indication member, in accordance with some described embodiments.

FIG. 17 illustrates a cross sectional view of an alternate embodiment of an indication member 430, in accordance with some described embodiments. As shown, the indication member 430 may include a first layer 432. The first layer 432 may include any feature or features previously described for a first layer. The second layer 434 may include ink material, including UV-fluorescent ink designed to illuminate or glow when exposed to UV light. However, the second layer 434 may be designed to "bleed" when exposed to liquid, and in this regard, the second layer 434 may include additional ink material as compared to prior embodiments. For example, when exposed to liquid, the second layer 434 may be carried away by the liquid. Further, when the indication member 430 is positioned in an electronic device (not shown), the second layer 434, when displaced by the liquid, may provide feedback to determine a location (or location) in which the liquid travels in the electronic device based upon the determined location of the second layer 434. This will be shown below.

Figure 18:
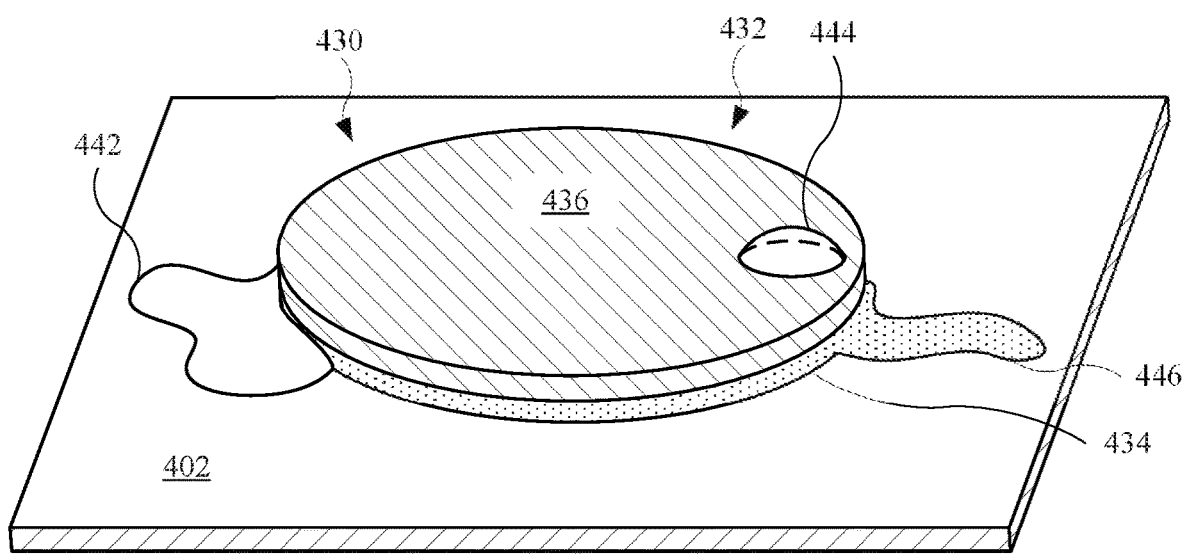
FIG. 18 illustrates an isometric view of the indication member shown in FIG. 17, further showing the indication member exposed to liquid, with a portion of the second layer carried away from the indication member by the liquid.

FIG. 18 illustrates an isometric view of the indication member 430 shown in FIG. 17, further showing the indication member 430 exposed to liquid, with a portion of the second layer 434 carried away from the indication member 430 by the liquid. The first layer 432 may dissolve or mix with the liquid. However, when the second layer 434 is exposed to the liquid, the second layer 434 may be transported. For example, when the second layer 434 is exposed to a first liquid source 442, the second layer 434 may interact with the first liquid source 442 to form a mixture 446 that includes the second layer 434 and the first liquid source 442. Accordingly, the second layer 434 may be carried away along a substrate 402, which may be part of an internal component of an electronic device and/or an enclosure of the electronic device. Also, the first layer 432 may receive liquid exposure from a second liquid source 444 that may interact with the first layer 432 and pass through to the second layer 434, causing a portion of the second layer 434 to rise to a top surface 436 of the first layer 432.

Figure 19:
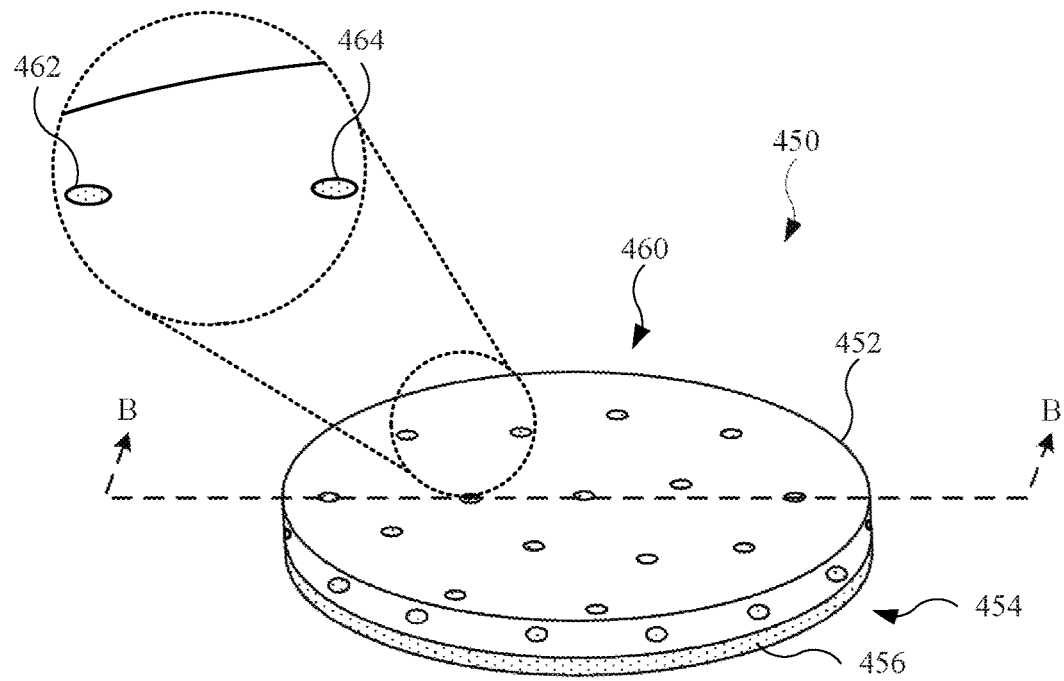
FIG. 19 illustrates an isometric view of an alternate embodiment of an indication member, showing the indication member having a layer with openings, with each of the openings filled with an ink material.

In some instances, an indication member is designed to accommodate additional ink material, as compared to the indication member 430 shown in FIGS. 17 and 18. For example, FIG. 19 illustrates an isometric view of an alternate embodiment of an indication member 450, showing the indication member 450 having a layer with openings 460, with each of the openings 460 filled with an ink material 456. As shown, the indication member 450 may include a first layer 452 positioned on a second layer 454, with the ink material 456 also used to form second layer 454. The ink material 456 may include an ink-based material, including ink powder. Also, the ink material that forms the second layer 454 may include UV-fluorescent ink.

The first layer 452 may include a paper, or paper-like, material that includes water-soluble or hydrophilic material properties (similar to previous embodiments). Moreover, in some embodiments, as shown in FIG. 19, the first layer 452 includes openings 460 that allow the first layer 452 to receive and carry the ink material 456, in additional to the ink material 456 that forms the second layer 454. As a result, the indication member 450 is capable of including additional ink material by way of the openings 460 in the first layer 452. Furthermore, in some instances, the dimensions of the indication member 450 need not change for the indication member 450 to hold additional ink material. In other words, the dimensions (i.e., height) of the second layer 454 does not need to increase for the indication member 450 to hold additional ink material (as compared to the indication member 330 in FIG. 17).

As shown in the enlarged view, the first layer 452 includes a first opening 462 and a second opening 464, each of which being representative of several, additional openings. Both the first opening 462 and the second opening 464 include the ink material 456. The openings 460 may be formed by several different means. For instance, the openings 460 may be formed by a cutting operation that forms several perforations in the first layer 452. As non-limiting examples, the cutting operation to the first layer 452 may include a blade or a laser-cutting tool. Also, the ink material 456 can be applied to the first layer 452, and in particular, the openings 460, by a printing operation, or a spraying operation, as non-limiting examples. Also, the openings 460 may form wells that receive the ink material 456. Although not shown, the indication member 450 may include an adhesive layer attached with the second layer 454 in order to secure the indication member 450 with an electronic device (not shown).

Figure 20:
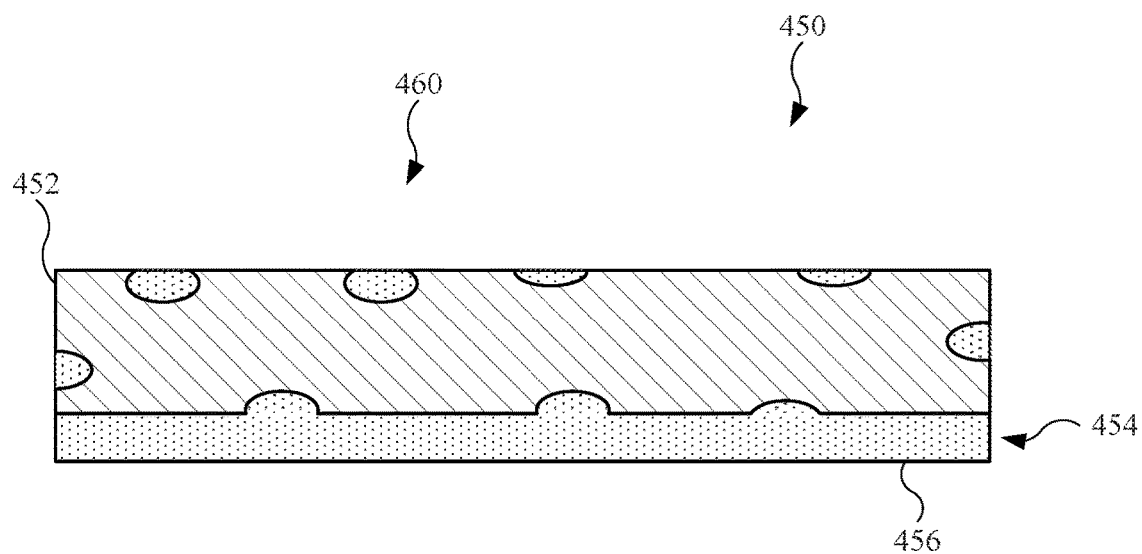
FIG. 20 illustrates a cross sectional view of the indication member shown in FIG. 19, taken along line B-B, further showing the openings of the first layer filled with the ink material.

FIG. 20 illustrates a cross sectional view of the indication member 450 shown in FIG. 19, taken along line B-B, further showing the openings 460 of the first layer 452 filled with the ink material 456. As shown, the ink material 456 not only resides in the second layer 454, but also throughout the first layer 452 in the openings 460 of the first layer 452. Also, at least some of the openings 460 can be formed on the lateral or side regions of the first layer 452, as shown in FIG. 20. In this configuration, when liquid (not shown) penetrates the indication member 450, the ink material 456, positioned in the openings 460 and forming the second layer 454, can be carried away from the indication member 450, in a manner similar to indication member 330 shown in FIG. 18. However, the amount of the ink material 456 may be greater, due in part to the openings 460 of the first layer 452 having the ink material 456.

Figure 21:
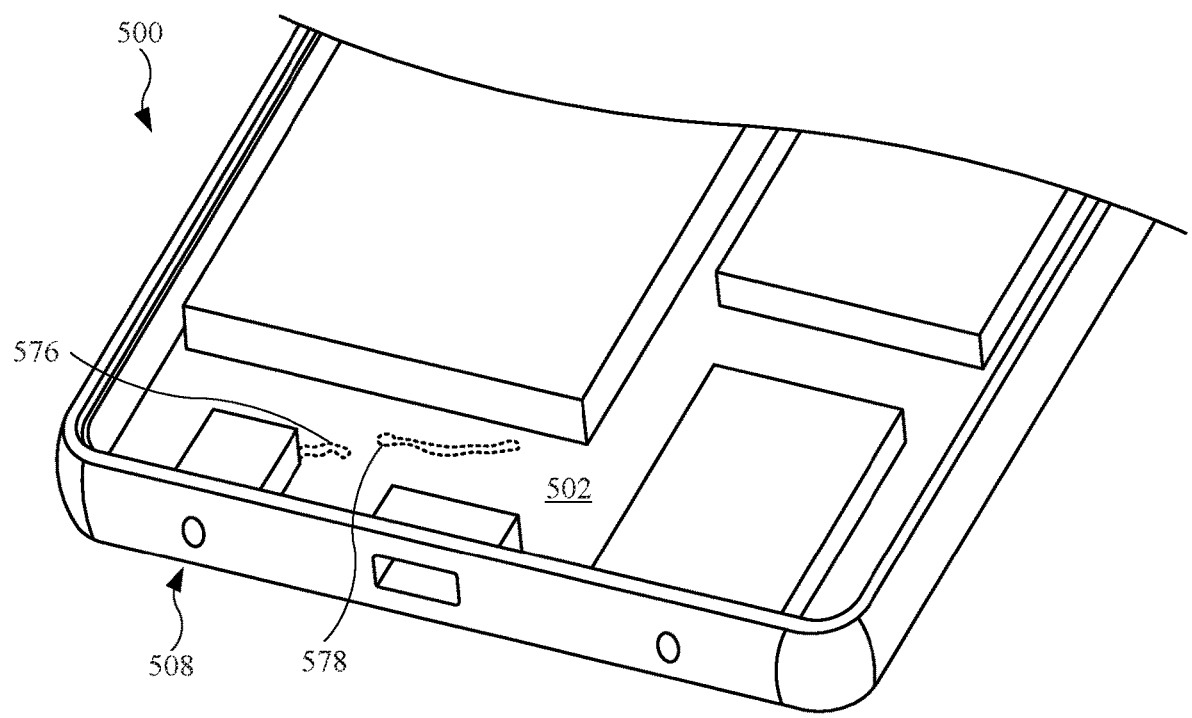
FIG. 21 illustrates a partial isometric view of an embodiment of an electronic device, subsequent to liquid exposure to several indication members, in accordance with some described embodiments.

FIG. 21 illustrates a partial isometric view of an embodiment of an electronic device 500, subsequent to liquid exposure to several indication members in the electronic device 500, in accordance with some described embodiments. The electronic device 500 may be similar to the electronic device 150 (shown in FIG. 1B), with the display assembly and the protective layer removed for purposes of illustration. The indication members described in FIG. 21 may include features of an indication member 430 (shown in FIG. 18). In this manner, the indication members may include a layer that is dissolved by the liquid, and another layer that is displaced due to liquid exposure. For example, as shown in FIG. 21, the electronic device 500 may include a first opening 508 that includes a first indication member (not shown). Subsequent to liquid exposure in the first opening 508, the first indication member may include a layer that combines with the liquid, resulting in a first mixture 576 disposed along an interior region of the electronic device 500, including an enclosure 502. Also, the enclosure 502 may include a second indication member such that when exposed to liquid, the second indication member combines with the liquid, resulting in a second mixture 578 disposed along an interior region of the electronic device 500. Although not shown, additional indication members are possible. As shown, the first mixture 576 and the second mixture 578 are represented by dotted lines, as these mixtures may be formed from a UV-fluorescent material generally not visible unless exposed to UV light.

Figure 22:
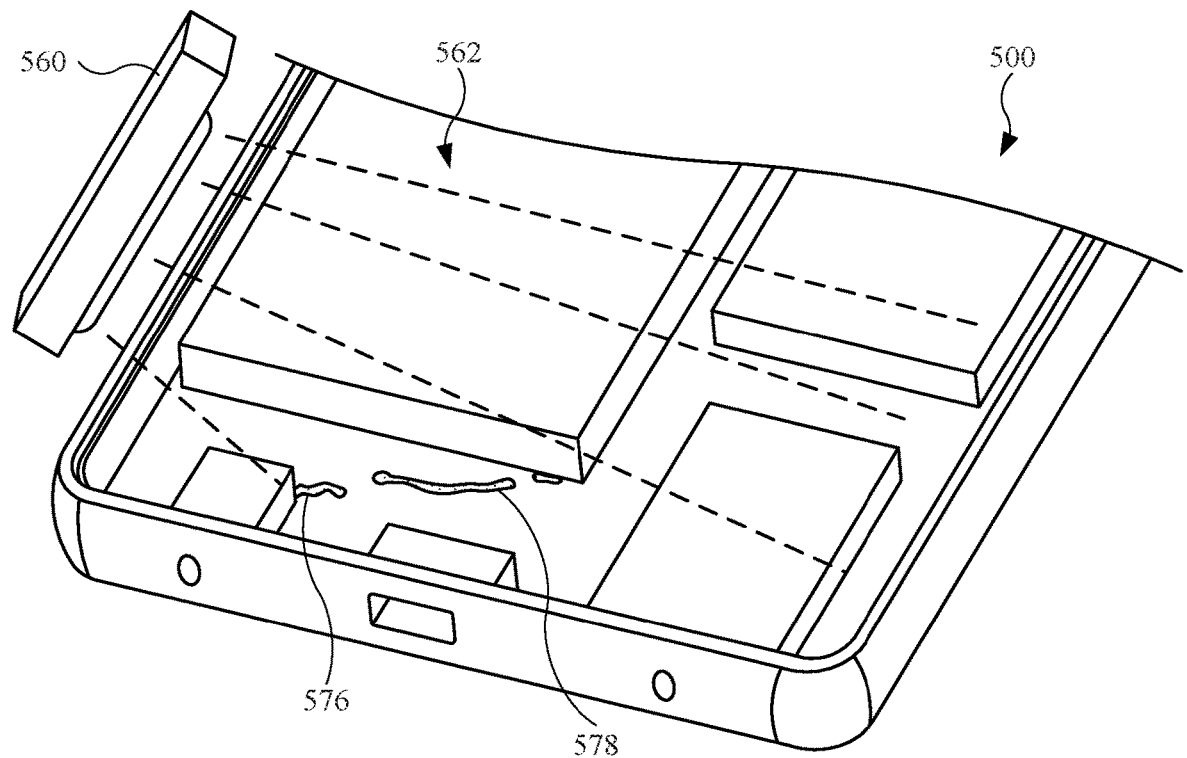
FIG. 22 illustrates a partial isometric view of the electronic device shown in FIG. 21, with the electronic device exposed to a light source.

FIG. 22 illustrates a partial isometric view of the electronic device 500 shown in FIG. 21, with the electronic device 500 exposed to a light source 560. The light source 560 may include a UV light source that emits UV light 562 to illuminate the first mixture 576 and the second mixture 578, causing the first mixture 576 and the second mixture 578 to illuminate and be visible, with the first mixture 576 and the second mixture 578 indicating that the electronic device is/was exposed to liquid ingress.

Based on the location of the respective mixtures, the ingress paths of the liquid may be determined. This information may be used to determine where liquid ingress is most likely to occur within the electronic device 500. Further, the mixtures may limit or prevent third parties from removing the mixtures, as the difficulty in removing the mixtures may be due in part to the lack of visibility of the mixtures (without using UV light). Also, when the mixture includes UV-fluorescent material that illuminates based on UV light with in a predetermined wavelength range, the mixtures may be even more difficult to detect.

Figure 23:
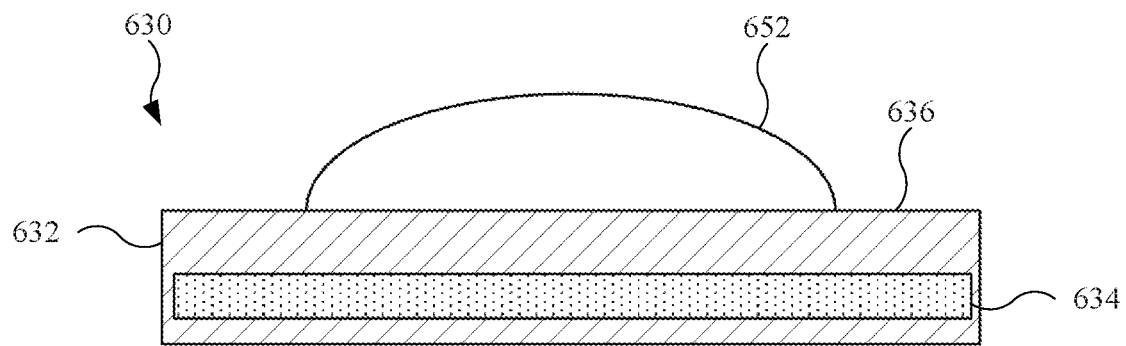
FIG. 23 illustrates a cross sectional view of an alternate embodiment of an indication member having an embedded layer, in accordance with some described embodiments.

FIG. 23 illustrates a cross sectional view of an alternate embodiment of an indication member 630 having an embedded layer, in accordance with some described embodiments. As shown, the indication member 630 may include a first layer 632, which may include any feature or feature previously described for a first layer. However, as shown in FIG. 23, the first layer 232 may include a second layer 234 embedded in the first layer 232. The second layer 234 may be embedded by processes such as impregnation, injection, or the like. Further, in some embodiments (not shown), the second layer 234 is positioned or sandwiched between two layers, each of which may include a layer similar to that of the first layer 632.

FIG. 23 further shows liquid 652 disposed on a top surface 636 of the indication member 630. Due in part to the hydrophilic properties of the first layer 632, the first layer 632 may allow liquid 652 to pass through the first layer 632 and interact with the second layer 634. For example, FIG. 19 illustrates a cross sectional view of the indication member 630 shown in FIG. 23, showing the liquid 652 penetrating through the first layer 632 to engage the second layer 634. The interaction between the first layer 632 and the liquid 652 causes the liquid 652 to engage the second layer 634, which in turn, causes the second layer 634 to rise or extend into the first layer 632.

Figure 24:
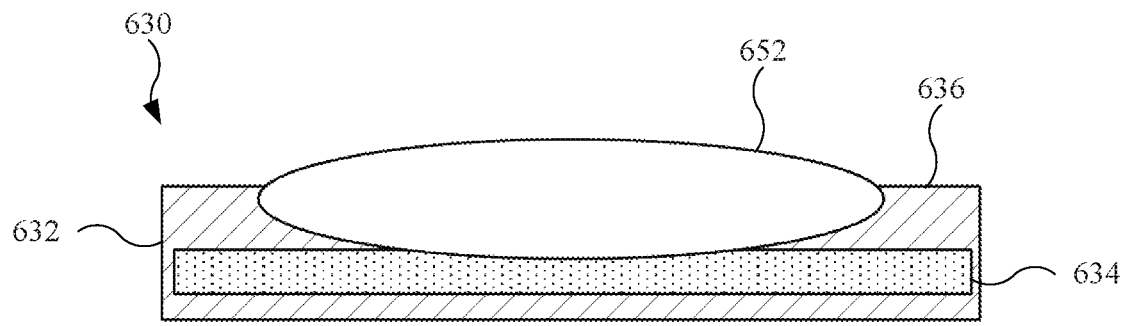
FIG. 24 illustrates a cross sectional view of the indication member shown in FIG. 23, showing the liquid penetrating through the first layer to engage the second layer.
Figure 25:
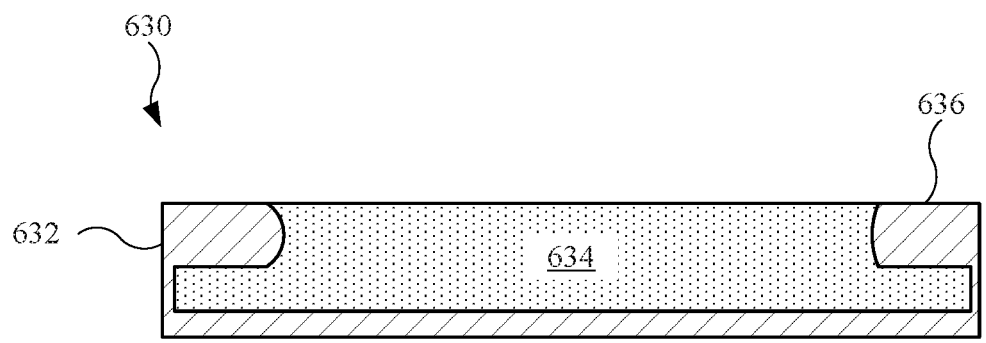
FIG. 25 illustrates a cross sectional view of the indication member shown in FIG. 24, showing the second layer passing through the first layer and extending to the top surface.

FIG. 25 illustrates a cross sectional view of the indication member 630 shown in FIG. 24, showing the second layer 634 passing through the first layer 632 and extending to the top surface 636. As shown, the second layer 634 may extend through the first layer 632 subsequent to interacting with the liquid 652 (shown in FIG. 24). Further, FIG. 25 shows portions of the second layer 634 rising to the top surface 636 in locations corresponding to the liquid exposure (from the liquid 652). By having an indication member 630 with an embedded layer (that is, the second layer 634), the indication member 630 may provide a complete encapsulation of the second layer 634, which may prevent instances "false triggering" of the second layer 634 being exposed at the top surface when the indication member 630 receives a relatively small, or insignificant, amount of liquid.

Figure 26:
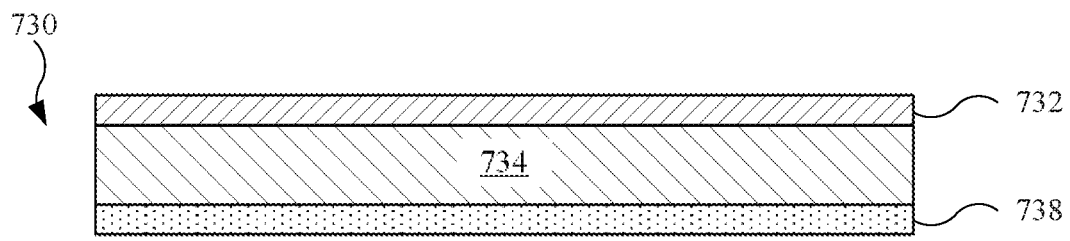
FIG. 26 illustrates a cross sectional view of an alternate embodiment of an indication member, in accordance with some described embodiments.

FIG. 26 illustrates a cross sectional view of an alternate embodiment of an indication member 730, in accordance with some described embodiments. As shown, the indication member 730 may include a first layer 732. In some embodiments, the first layer 732 is formed from an ink material designed to give the indication member 730 a cosmetic or aesthetic appearance. For example, the first layer 732 may include an appearance (such as a color) similar to that of a component (not shown) on which the indication member 730 is positioned. Also, the first layer 732 may include water-soluble ink. The indication member 730 may also include a second layer 734 formed from paper, or a paper-like material, as an example. In this regard, the second layer 734 may include a water-soluble or hydrophilic material. The indication member 730 may further include a third layer 738 formed from ink or an ink-based material. In some embodiments, the third layer 738 includes a UV-fluorescent ink designed to illuminate or glow when exposed to UV light. Based on its position relative to the first layer 732 and the third layer 738, the second layer 734 may also be referred to as an intermediate layer.

Figure 27:
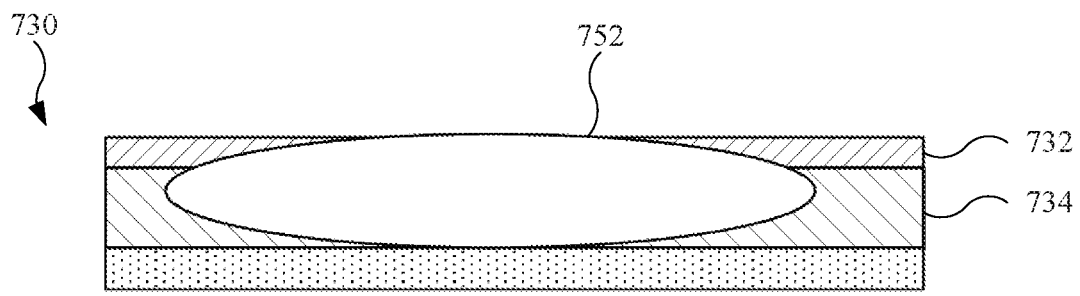
FIG. 27 illustrates a cross sectional view of the indication member shown in FIG. 26, showing the liquid extending through the first layer and the second layer.
Figure 28:
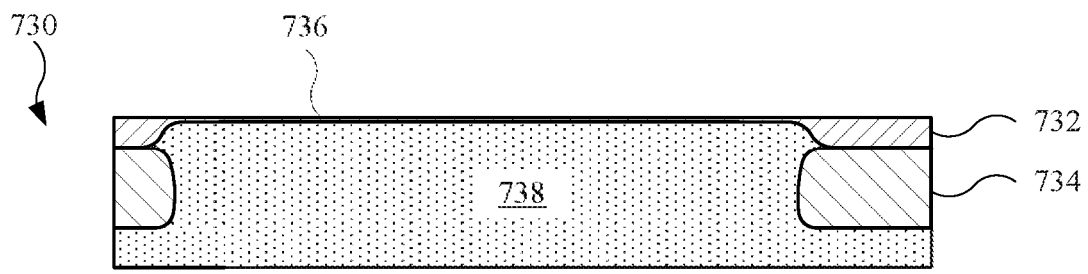
FIG. 28 illustrates a cross sectional view of the indication member shown in FIG. 27, showing a portion of the third layer extending through the second layer and into the first layer.

FIG. 27 illustrates a cross sectional view of the indication member 730 shown in FIG. 26, showing liquid extending through the first layer 732 and the second layer 734. As shown, liquid 752 may pass through the first layer 732 and the second layer 734. FIG. 28 illustrates a cross sectional view of the indication member 730 shown in FIG. 27, showing a portion of the third layer 738 extending through the second layer 734 and into the first layer 732. Subsequent to the liquid 752 contacting the third layer 738, the third layer 738 may rise through and into the first layer 732 and the second layer 734 in a location corresponding to the location of the liquid 752 (shown in FIG. 27). While the third layer 738 may extend into the first layer 732, the third layer may not fully penetrate the first layer 732, and accordingly, does not reach a top surface 736 of the indication member 730. However, the penetration of the third layer 738 into the first layer 732 may be sufficient for the third layer 738 to illuminate or glow when exposed to UV light.

Figure 29:
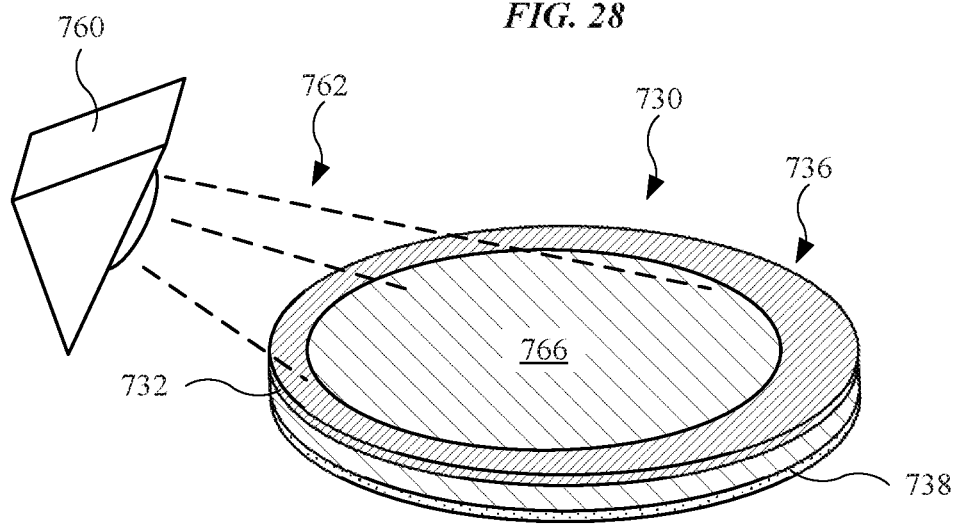
FIG. 29 illustrates an isometric view of the indication member shown in FIG. 28, showing the indication member illuminating in certain locations.

For example, FIG. 29 illustrates an isometric view of the indication member 730 shown in FIG. 28, showing the indication member 730 illuminating in certain locations. As shown, a light source 760, which may include a UV light source, emits UV light 762 to illuminate the indication member 730. In particular, an illuminated portion 766 of the indication member 730 may correspond to a location in which the liquid 752 (shown in FIG. 27) contacts the top surface 736. In this regard, the indication member 730 may illuminate to indicate liquid exposure, even when the top surface 736 of the indication member 730 is undisturbed. Accordingly, the first layer 732 may maintain an appearance similar to that of a component on which the indication member 730 is positioned. Further, when the light source 760 is turned off, the indication member 730 has no indication of liquid ingress, as the illuminated portion 766 is no longer visible and the first layer 732 maintains its appearance. In some instances, the liquid 752 (shown in FIG. 27) may entirely cover the top surface 736, causing the illuminated portion 766 to entirely encompass the top surface 736. This may also provide an indication of liquid exposure as the appearance of the first layer 732 (prior to liquid exposure) is no longer present.

Figure 30:
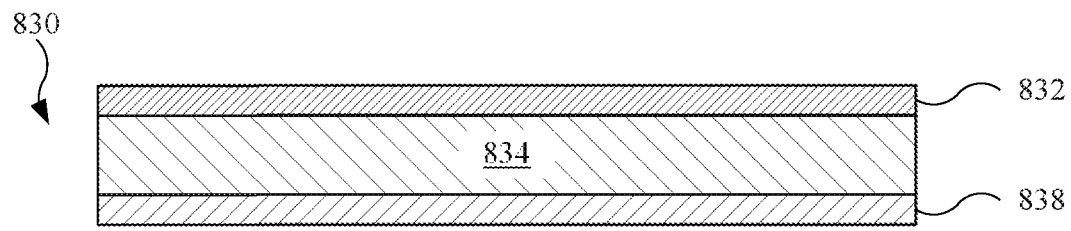
FIG. 30 illustrates a cross sectional view of an alternate embodiment of an indication member, in accordance with some described embodiments.

While several prior embodiments include a UV-fluorescent material and a UV light source to detect the UV-fluorescent material, some indication members may not require a UV light source. For example, FIG. 30 illustrates a cross sectional view of an alternate embodiment of an indication member 830, in accordance with some described embodiments. As shown, the indication member 830 may include a first layer 832. In some embodiments, the first layer 832 is formed from an ink material designed to give the indication member 830 a cosmetic or aesthetic appearance. For example, the first layer 832 may include an appearance (such as a color) similar to that of a component on which the indication member 830 is positioned. Also, the first layer 832 may include water-soluble ink. The indication member 830 may also include a second layer 834 formed from paper, or a paper-like material. In this regard, the second layer 834 may include a water-soluble or hydrophilic material. The indication member 830 may further include a third layer 838 formed from ink or an ink-based material. Accordingly, based on its position relative to the first layer 832 and the third layer 838, the second layer 834 may also be referred to as an intermediate layer.

In some embodiments, the third layer 838 includes a color different from that of the first layer 832. Further, in response to liquid exposure, the third layer 838, or portions thereof, may interact and mix with the first layer 832 causing an alteration to the first layer 832. This alteration may include a color distinguishable from the color of the first layer 832 and a color of the third layer 838. This will be shown below.

Figure 31:
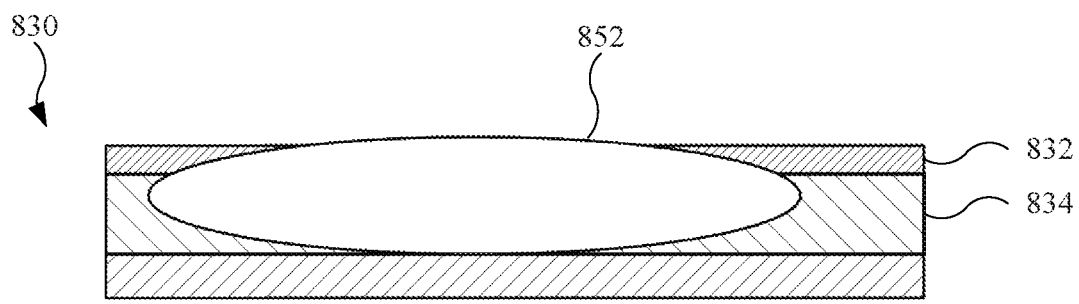
FIG. 31 illustrates a cross sectional view of the indication member shown in FIG. 30, showing the liquid extending through the first layer and the second layer.
Figure 32:
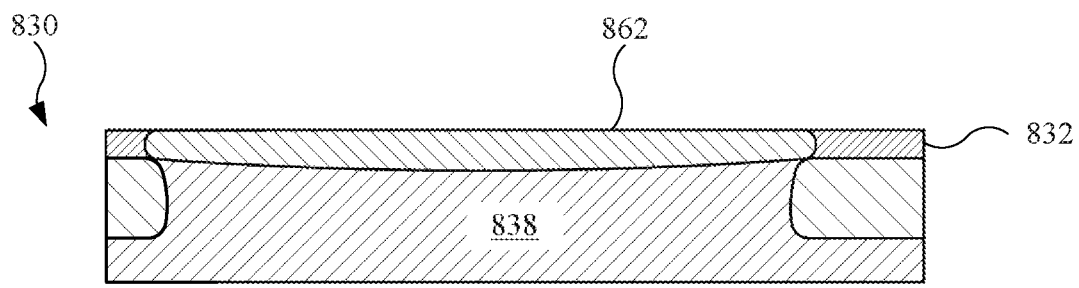
FIG. 32 illustrates a cross sectional view of the indication member shown in FIG. 31, showing a portion of the third layer extending through the second layer and into the first layer.

FIG. 31 illustrates a cross sectional view of the indication member 830 shown in FIG. 30, showing liquid extending through the first layer 832 and the second layer 834. As shown, liquid 852 may pass through the first layer 832 and the second layer 834 to reach the third layer 838. FIG. 32 illustrates a cross sectional view of the indication member 830 shown in FIG. 31, showing a portion of the third layer 838 extending through the second layer 834 and into the first layer 832. Subsequent to the liquid 852 contacting the third layer 838, the third layer 838 may rise through and into the first layer 832 and the second layer 834 in a location (or locations) corresponding to the location of the liquid 852 (shown in FIG. 31). Further, the first layer 832 and the third layer 838 may mix to define a mixture 862. The mixture 862 may include an appearance that includes a blended appearance of the first layer 832 and the third layer 838. For example, the first layer 832 may include black and the third layer 838 may include red, and as a result, the mixture 862 may include dark red or burgundy color visibly distinguishable from the black color defining the first layer 832.

Figure 33:
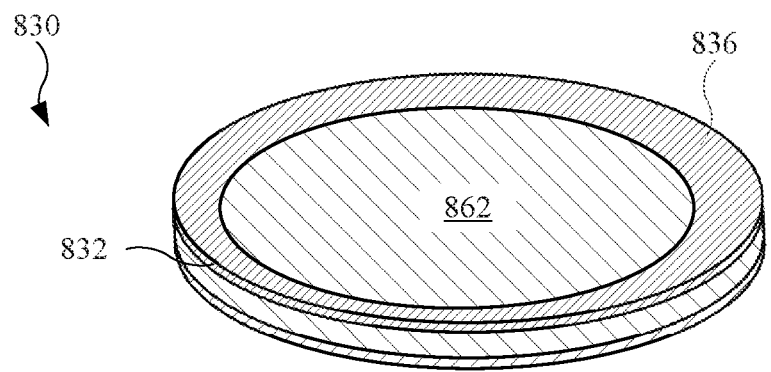
FIG. 33 illustrates an isometric view of the indication member shown in FIG. 32, showing alterations of the indication member defined by the first mixture and the second mixture.

FIG. 33 illustrates an isometric view of the indication member 830 shown in FIG. 32, showing alterations of the indication member 830 defined by the mixture 862. The mixture 862 may include an appearance (including color) at a top surface 836 of the indication member 830 that is noticeably different from that of the first layer 832, and the indication member 830 may provide an indication of liquid exposure based on the mixture 862. In some instances, the liquid 852 (shown in FIG. 31) may entirely cover the top surface 836, causing the mixture 862 to entirely encompass the top surface 836. This may also provide an indication of liquid exposure as the appearance of the first layer 832 (prior to liquid exposure) is no longer present.

Figure 34:
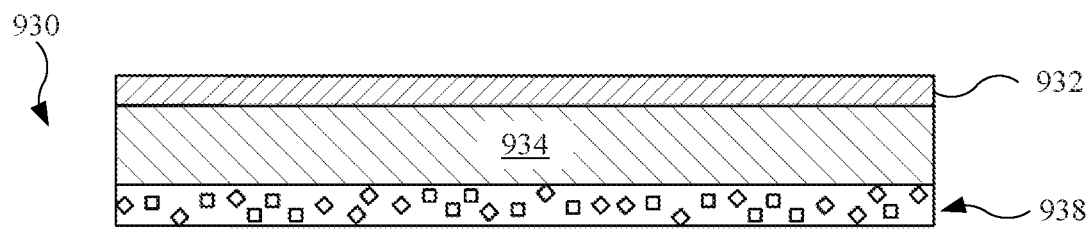
FIG. 34 illustrates a cross sectional view of an alternate embodiment of an indication member having a compound that defines at least one of the layers, in accordance with some described embodiments.

FIG. 34 illustrates a cross sectional view of an alternate embodiment of an indication member 930 having a compound that defines at least one of the layers, in accordance with some described embodiments. As shown, the indication member 930 may include a first layer 932. In some embodiments, the first layer 932 is formed from an ink material designed to give the indication member 930 a cosmetic or aesthetic appearance. For example, the first layer 932 may include an appearance (such as a color) similar to that of a component on which the indication member 930 is positioned. Also, the first layer 932 may include water-soluble ink. The indication member 930 may also include a second layer 934 formed from paper, or a paper-like material. In this regard, the second layer 934 may include a water-soluble or hydrophilic material. The indication member 930 may further include a third layer 938 formed from salt or a salt-based material. Based on its position relative to the first layer 932 and a third layer 938 (discussed below), the second layer 934 may also be referred to as an intermediate layer.

The third layer 938 may include a material formed from bleached salts, including dried sodium hypochlorite. Further, in response to liquid exposure, the third layer 938, or portions thereof, may interact and mix with the first layer 932 causing an alteration to the first layer 932. This alteration may include a color distinguishable from the color of the first layer 932. This will be shown below.

Figure 35:
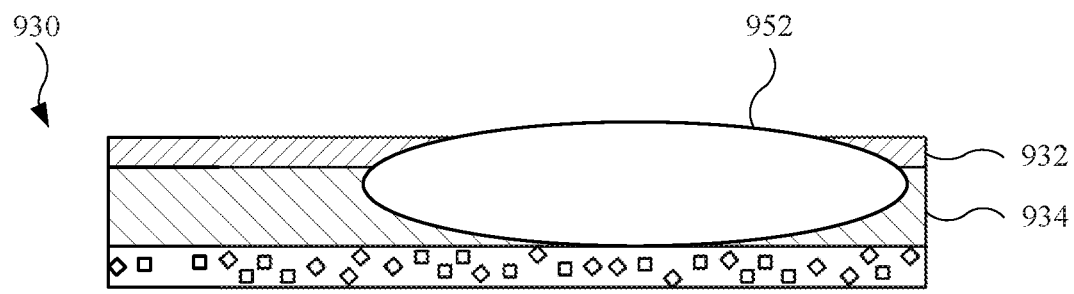
FIG. 35 illustrates a cross sectional view of the indication member shown in FIG. 34, showing the liquid extending through the first layer and the second layer.
Figure 36:
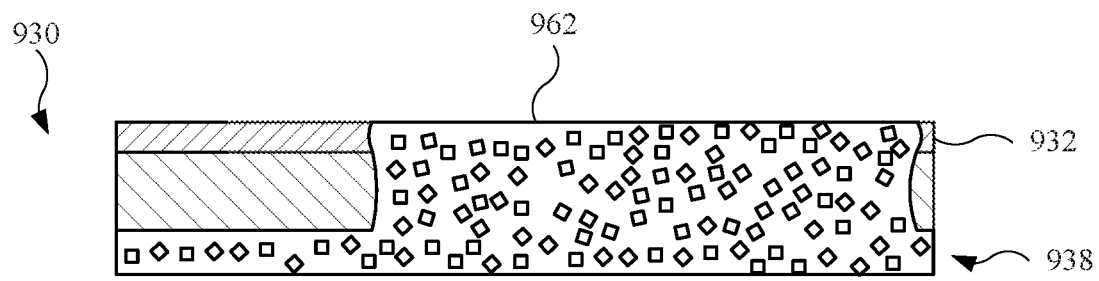
FIG. 36 illustrates a cross sectional view of the indication member shown in FIG. 35, showing a portion of the third layer extending through the second layer and into the first layer.

FIG. 35 illustrates a cross sectional view of the indication member shown in FIG. 34, showing liquid extending through the first layer 932 and the second layer 934. As shown, liquid 952 may pass through the first layer 932 and the second layer 934 to reach the third layer 938. FIG. 36 illustrates a cross sectional view of the indication member 930 shown in FIG. 35, showing a portion of the third layer 938 extending through the second layer 934 and into the first layer 932. Subsequent to the liquid 952 contacting the third layer 938, the third layer 938 may rise through and into the first layer 932 and the second layer 934 in a location (or locations) corresponding to the location of the liquid 952 (shown in FIG. 35). Further, the first layer 932 may mix with the third layer 938, causing a bleached appearance at the first layer 932. As shown, the first layer 932, as a result of the mixture, may include a bleached region 962. The first layer 932 may include an appearance (such as a black color), while the bleached region 962 may cause an appearance (such as gray or white) visibly distinguishable from the appearance defining the first layer 932.

Figure 37:
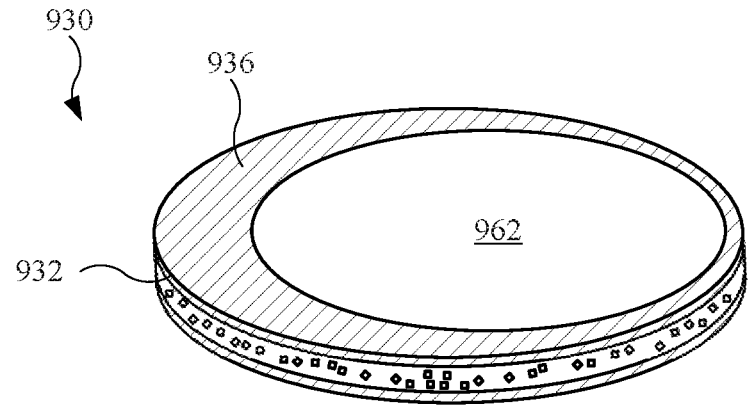
FIG. 37 illustrates an isometric view of the indication member shown in FIG. 36, showing alterations of the indication member defined by the first bleached.

FIG. 37 illustrates an isometric view of the indication member 930 shown in FIG. 36, showing alterations of the indication member 930 defined by the bleached region 962. The bleached region 962 may include an appearance (including color) at a top surface 936 of the first layer 932 that is noticeably different from that of the first layer 932, and the indication member 930 may provide an indication of liquid exposure based on the bleached region 962. In some instances, the liquid 952 (shown in FIG. 35) may entirely cover the top surface 936, causing the bleached region 962 to entirely encompass the top surface 936. This may also provide an indication of liquid exposure as the appearance of the first layer 932 (prior to liquid exposure) is no longer present.

Figure 38:
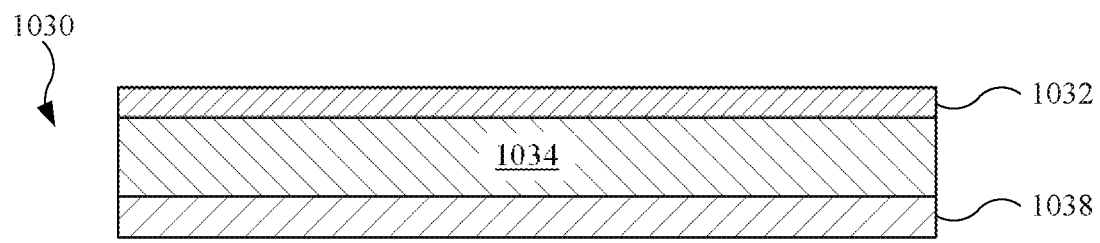
FIG. 38 illustrates a cross sectional view of an alternate embodiment of an indication member, in accordance with some described embodiments.

FIG. 38 illustrates a cross sectional view of an alternate embodiment of an indication member 1030, in accordance with some described embodiments. As shown, the indication member 1030 may include a first layer 1032. In some embodiments, the first layer 1032 is formed from an ink material designed to give the indication member 1030 a cosmetic or aesthetic appearance. For example, the first layer 1032 may include an appearance (such as a color) similar to that of a component on which the indication member 1030 is positioned. Also, the first layer 1032 may include water-soluble ink. The indication member 1030 may also include a second layer 1034 formed from paper, or a paper-like material. In this regard, the second layer 1034 may include a water-soluble or hydrophilic material. The indication member 1030 may further include a third layer 1038 formed from ink or an ink-based material. Based on its position relative to the first layer 1032 and the third layer 1038, the second layer 1034 may also be referred to as an intermediate layer.

The third layer 1038 may include a material formed from a hydrochromatic ink designed to disappear (or at least not appear visible) when exposed to liquids, such as water. Further, in response to liquid exposure, the third layer 1038, or portions thereof, may interact and mix with the first layer 1032 causing an alteration at the first layer 1032. This alteration may include an appearance distinguishable from that of the first layer 1032.

Figure 39:
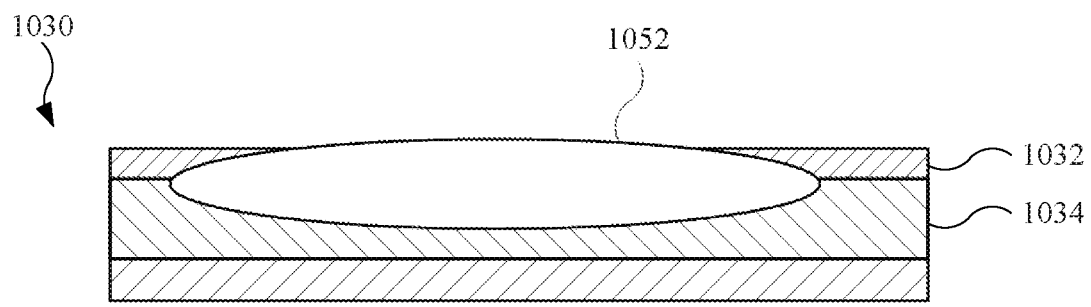
FIG. 39 illustrates a cross sectional view of the indication member shown in FIG. 38, showing liquid extending through the first layer and the second layer.
Figure 40:
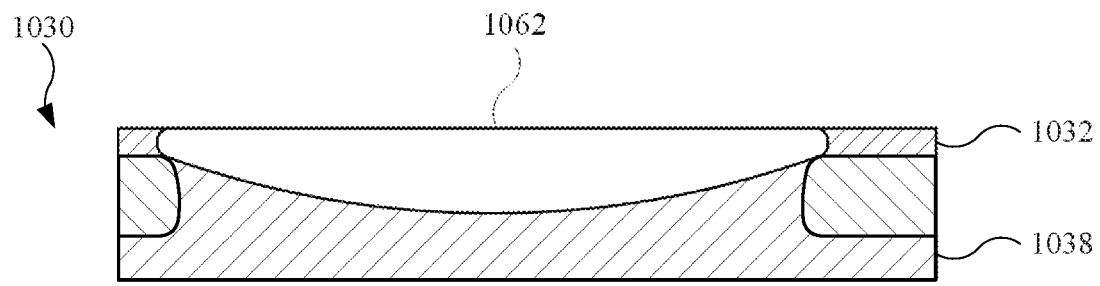
FIG. 40 illustrates a cross sectional view of the indication member shown in FIG. 39, showing a portion of the third layer extending through the second layer and into the first layer.

FIG. 39 illustrates a cross sectional view of the indication member 1030 shown in FIG. 38, showing liquid extending through the first layer 1032 and the second layer 1034 to reach the third layer 1038. As shown, liquid 1052 may pass through the first layer 1032 and the second layer 1034. FIG. 40 illustrates a cross sectional view of the indication member 1030 shown in FIG. 39, showing a portion of the third layer 1038 extending through the second layer 1034 and into the first layer 1032. Subsequent to the liquid 1052 contacting the third layer 1038, the third layer 1038 may rise through and into the first layer 1032 and the second layer 1034 in a location (or locations) corresponding to the location of the liquid 1052 (shown in FIG. 39). Further, the first layer 1032 may mix with the third layer 1038, causing a portion of the first layer 1032 to change in appearance. As shown, the first layer 1032, as a result of the mixture, may include a clear region 1062 defined by a relative absence of color as compared to that of the first layer 1032. As an example, the first layer 1032 may include a black appearance, while the clear region 1062 may cause a generally white appearance visibly distinguishable from the black color defining the first layer 1032. Further, when the first layer 1032 is a color other than black, the clear region 1062 may nonetheless be visibly distinguishable from the first layer 1032.

Figure 41:
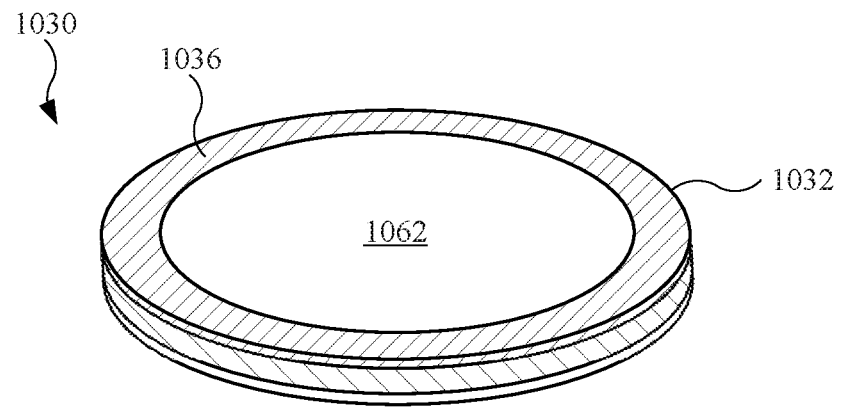
FIG. 41 illustrates an isometric view of the indication member shown in FIG. 40, showing alterations of the indication member defined by the clear region.

FIG. 41 illustrates an isometric view of the indication member shown in FIG. 40, showing alterations of the indication member 1030 defined by the clear region 1062. The clear region 1062 may include an appearance (including color) at a top surface 1036 of the first layer 1032 that is noticeably different from that of the first layer 1032, and the indication member 1030 may provide an indication of liquid exposure based on the clear region. In some instances, the liquid 1052 (shown in FIG. 39) may entirely cover the top surface 1036, causing the clear region 1062 to entirely encompass the top surface 1036. This may also provide an indication of liquid exposure as the appearance of the first layer 1032 (prior to liquid exposure) is no longer present.

Figure 42:
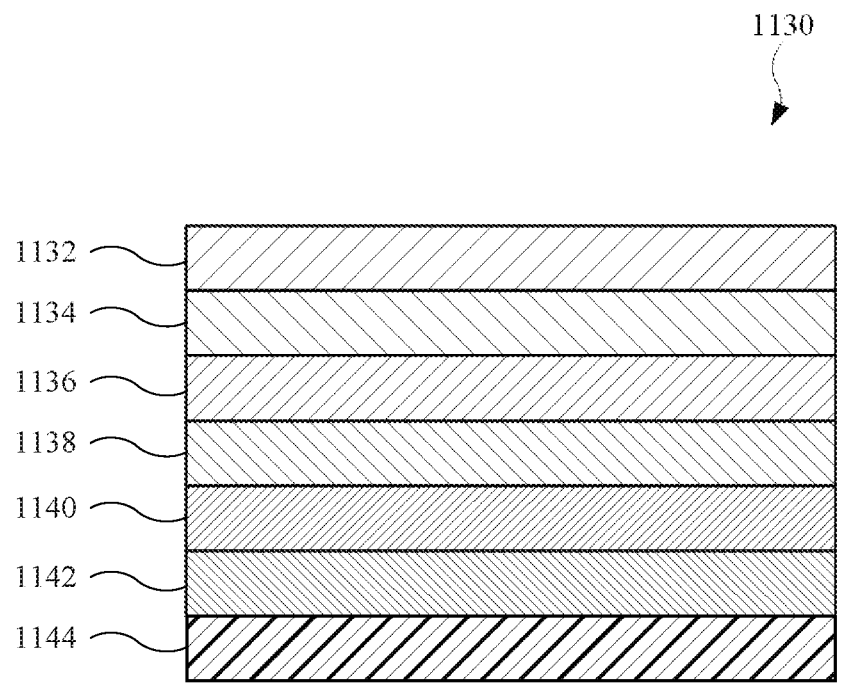
FIG. 42 illustrates a cross sectional view of an alternate embodiment of an indication member having several additional layers, in accordance with some described embodiments.

FIG. 42 illustrates a cross sectional view of an alternate embodiment of an indication member 1130 having several additional layers, in accordance with some described embodiments. Although a cross section is shown, the indication member 1130 may include a circular, oblong, or other polygonal shape. As shown, the indication member 1130 may include a first layer 1132. The first layer 1132 may include a fluorescent coating that includes a matt and blue appearance. In this regard, the indication member 1130 may be readily located by the appearance of the first layer 1132, and in particular, when the first layer 1132 is exposed to UV light.

The indication member 1130 may further include a second layer 1134. The second layer 1134 may include a PET film, and include a dark appearance representative of a black appearance. The second layer 1134 is designed to provide the indication member 1130 with a water-resistant layer. For example, the second layer 1134 may prevent liquid from that contacts the first layer 1132 from further penetrating through the indication member 1130.

The indication member 1130 may further include a third layer 1136. The third layer 1136 may include an adhesive material designed to secure the second layer 1134 and a fourth layer 1138 (discussed below) together and maintain these layers with the indication member 1130. In some embodiments, the third layer 1136 includes a pressure sensitive adhesive ("PSA"), including an acrylic PSA.

The indication member 1130 may further include a fourth layer 1138. The fourth layer 1138 may include a paper material, including a soluble paper. In this regard, the fourth layer 1138 may include a water-soluble or hydrophilic material, designed to receive liquid. Further, in some embodiments, the fourth layer 1138 may not only absorb liquid, but also the fourth layer 1138 may expand in one or more dimensions when the fourth layer 1138 absorbs liquid. For example, the fourth layer 1138 may act in a manner similar to that of the second layer 264, shown in FIGS. 5-7. Accordingly, the fourth layer 1138 may provide an indication of liquid ingress into an electronic device (not shown), as the indication member 1130 changes its shaped based on the expansion of the fourth layer 1138.

The indication member 1130 may further include a fifth layer 1140. The fifth layer 1140 may include an ink material, including an ink-based liquid or an ink powder. Further, in some embodiments, the fifth layer 1140 includes a fluorescent ink material. When the fifth layer 1140 include fluorescent ink, the indication member 1130 may illuminate when exposed to UV light. Further, when the fourth layer 1138 is exposed to liquid, the fourth layer 1138 may absorb, or at least partially absorb, the fifth layer 1140. And, when the fourth layer 1138 expends due to liquid absorption, the fourth layer 1138 may carry portions of the fifth layer 1140 in multiple directions in accordance with the expansion of the fourth layer 1138. Then, when the indication member 1130 is exposed to UV light, the fifth layer 1140 may illuminate (and become visible) and illuminate the fourth layer 1138 that is UV-illuminated. This, along with the expansion of the fourth layer 1138 (when applicable), provides an indication of liquid exposure to the indication member 1130.

The indication member 1130 may further include a sixth layer 1142. The sixth layer 1142 may include an adhesive material designed to secure the fifth layer 1140 and a seventh layer 1144 (discussed below) together and maintain these layers with the indication member 1130. In some embodiments, the sixth layer 1142 includes a pressure sensitive adhesive ("PSA"), including an acrylic PSA. Further, in some embodiments, the sixth layer 1142 includes a dark appearance representative of a black appearance. The appearance of the sixth layer 1142 may also shield the fifth layer 1140.

The indication member 1130 may further include a seventh layer 1144. The seventh layer 1144 may cover the sixth layer 1142. In this regard, when the sixth layer 1142 includes an adhesive layer, the seventh layer 1144 may prevent the sixth layer 1142 from prematurely adhering to a surface, such as an enclosure or component of an electronic device (not shown). The seventh layer 1144 may be removed from the indication member 1130 when the indication member 1130 is ready to secure with a surface.

In instances when the indication member 1130 is fully immersed in liquid, some layers may erode or may be carried away from the remaining layers of the indication member 1130. For example, the first layer 1132 and the second layer 1134 may be carried away by the flow of the liquid. However, even in these instances, at least some of the fourth layer 1138 may remain as it is adhesively secured with the third layer 1136. This may also retain the fifth layer 1140 with the indication member 1130 and allow at least some of the fifth layer 1140 to be absorbed by the fourth layer 1138. As such, the indication member 1130 may nonetheless provide an indication of liquid exposure when one or more layers are removed.

Figure 43:
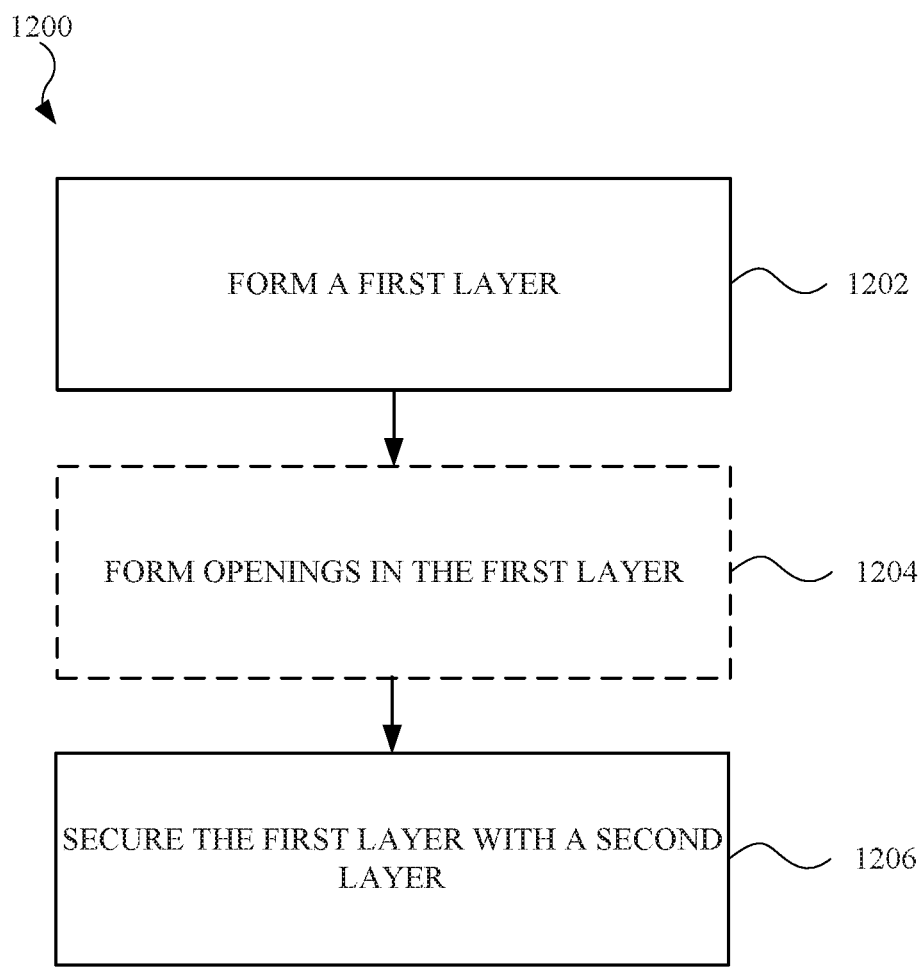
FIG. 43 illustrates a flowchart showing a method for forming an indication member, in accordance with some described embodiments.

FIG. 43 illustrates a flowchart 1200 showing a method for forming an indication member, in accordance with some described embodiments. The indication member may be used to provide an indication of liquid exposure in an electronic device. In this regard, when exposed to sufficient liquid, the indication member may change its appearance, with the appearance change corresponding to liquid ingress in the electronic device. For example, the indication may include an ink material positioned below, and/or embedded, in a layer of material. The ink material may become visible after sufficient liquid exposure to the indication member. Accordingly, the indication member provides the indication by way of the ink material.

In step 1202, a first layer is formed. The first layer may include a paper, or paper-like, material that includes water-soluble or hydrophilic material properties. Further in some embodiments, when the paper material is used, the first layer is designed to expand in multiple directions when exposed to liquid. For example, the first layer may expand radially outward, and may also expand in a direction perpendicular to the radially outward direction (such as vertically). In addition to the ink material (discussed below), the expansion of the first layer may provide an indication of liquid exposure or liquid ingress in an electronic device. Also, in some embodiments, a water-resistant layer is applied over the first layer such that liquid penetration into the indication member occurs at the lateral or side regions of the indication member.

Optionally, in step 1204, several openings are formed in first layer. The openings formed in the first layer may include perforations formed by a cutting operation, as a non-limiting example. The openings are designed to receive and carry a material, such as an ink material.

In step 1206, a second layer is secured with the first layer. The second layer may include an ink (or ink-based) material. In some embodiments, the ink material includes UV-fluorescent ink that is visible (to the human eye) only when exposed to UV light from a UV light source. In some embodiments, the ink material is colored, and accordingly, provides a visible change in appearance (without a UV light source required) to the indication member when the indication member is exposed to liquid.

Figure 44:
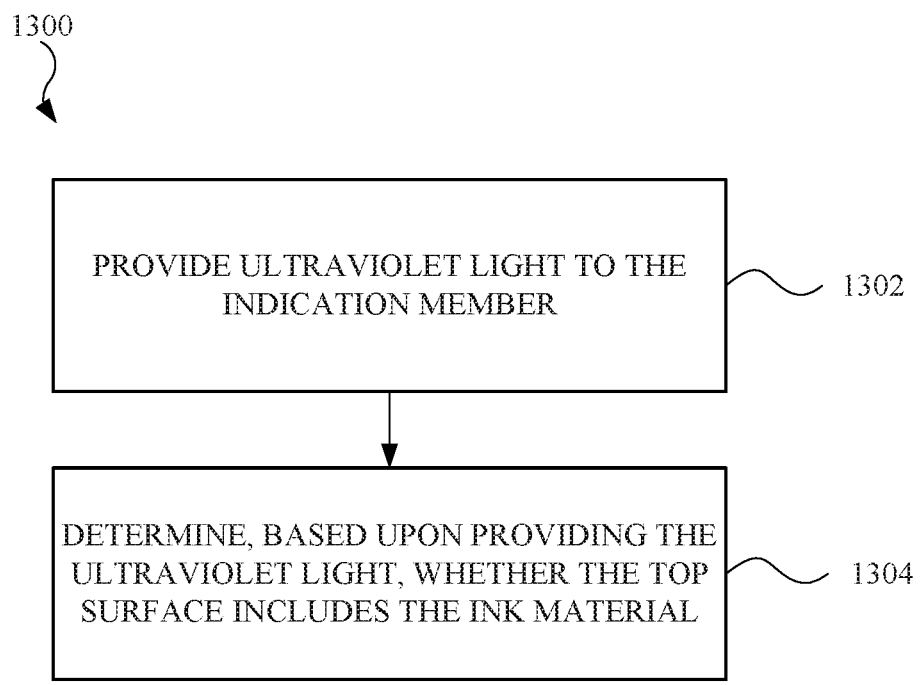
FIG. 44 illustrates a flowchart showing a method for detecting liquid ingress in an electronic device, in accordance with some described embodiments.

FIG. 44 illustrates a flowchart 1300 showing a method for detecting liquid ingress in an electronic device that includes an indication member that includes an ink material and a layer having a top surface that covers the ink material, in accordance with some described embodiments. In step 1302, a UV light source is provided to the indication member. The ink material may be detectable when exposed to the ultraviolet light source. Also, the ink material may be configured to rise to the top surface when exposed to the liquid ingress. In some embodiments, the ink material includes UV-fluorescent material designed to illuminate or glow in response to UV light. Further, the ink material may include UV-fluorescent material designed to illuminate or glow only in response to UV light having a wavelength in a predetermined range of wavelengths.

In step 1304, a determination, based upon providing the ultraviolet light source, is made whether the top surface includes the ink material. The ink material may pass through one or more layers of material defining the indication member. In this regard, the indication member, in addition to a layer having UV-fluorescent ink, may include a layer that includes a water-soluble or hydrophilic material formed from a paper-based material or an ink-based material. The indication member may further include an additional layer that includes a paper-like material. Also, in some cases, the UV-fluorescent ink is disposed on an uppermost layer of the indication member. In other cases, the UV-fluorescent ink is disposed below an uppermost layer of the indication member.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. An indication member for determining a presence of liquid in a consumer electronic device, the indication member comprising:
   a layer comprising a porous region that defines an exterior surface of the indication member; and
   an ink material engaging the layer, wherein:
   the ink material migrates through the porous region to a location at the exterior surface when the liquid is present at the location; and
   the ink material fluoresces at the location when exposed to ultraviolet light.

2. The indication member of claim 1, wherein:
   the layer defines a second surface opposite the exterior surface; and
   the ink material is at least partially embedded in the layer between the exterior surface and the second surface.

3. The indication member of claim 1, wherein the ink material is disposed in a predetermined pattern.

4. The indication member of claim 3, wherein the migration of the ink material to the location alters the predetermined pattern.

5. The indication member of claim 1, wherein the ink material, when exposed to the liquid, is carried away from the layer.

6. The indication member of claim 1, wherein the layer expands in a first direction and a second direction that is perpendicular to the first direction when the liquid is present on the layer.

7. An electronic device, comprising:
   an enclosure defining an internal cavity; and
   an indication member carried by the enclosure and disposed in the internal cavity, the indication member defining an exterior surface and comprising an ink material that fluoresces at a location of a liquid at the exterior surface when the exterior surface is exposed to ultraviolet light.

8. The electronic device of claim 7, wherein the indication member comprises a layer disposed over the ink material, the layer comprising a hydrophilic material that allows the liquid to pass through the layer at the location and cause the ink material to pass through the layer at the location.

9. The electronic device of claim 8, wherein the ink material is carried away from the layer when exposed to the liquid.

10. The electronic device of claim 7, further comprising an internal component comprising a color, wherein the portion of the indication member defining the exterior surface comprises the color.

11. The electronic device of claim 7, wherein the indication member comprises a layer defining the top surface and the ink material defines a pattern at the top surface.

12. The electronic device of claim 11, wherein the pattern is altered at the location of the liquid.

13. A method for detecting a liquid ingress event in an electronic device comprising an indication member comprising an ink material and a layer defining an exterior surface that covers the ink material, the method comprising:
   exposing the exterior surface to ultraviolet light, wherein the ink material fluoresces at a location on the exterior surface that has been contacted by the liquid when exposed to the ultraviolet light; and
   determining whether the exterior surface includes the ink material based at least partially on the fluorescence of the ink material at the location.

14. The method of claim 13, wherein determining whether the exterior surface includes the ink material comprises determining whether a pattern of the exterior surface is altered.

15. The method of claim 14, wherein the pattern and the ink material fluoresce when exposed to ultraviolet light.

16. The method of claim 14, wherein the pattern comprises an indicium or a grid.

17. The method of claim 13, further comprising determining whether the ink material is carried away from the indication member by the liquid.

18. The method of claim 13, wherein exposing the exterior surface to ultraviolet light comprises exposing the exterior surface to ultraviolet light of a predetermined wavelength and the ink material comprises an ultraviolet fluorescent ink that fluoresces when exposed to the light of the predetermined wavelength.

* * * * *